US008580843B2

(12) United States Patent
Tjalkens et al.

(10) Patent No.: US 8,580,843 B2
(45) Date of Patent: Nov. 12, 2013

(54) USE OF DIINDOLYLMETHANE (DIM) COMPOUNDS AND DERIVATIVES AS NEUROPROTECTIVE AGENTS

(75) Inventors: Ronald B. Tjalkens, Fort Collins, CO (US); Stephen Safe, College Station, TX (US)

(73) Assignees: Colorado State University Research Foundation, Fort Collins, CO (US); The Texas A&M University System, College Station, TX (US)

( * ) Notice: Subject to any disclaimer, the term of this patent is extended or adjusted under 35 U.S.C. 154(b) by 739 days.

(21) Appl. No.: 12/575,415

(22) Filed: Oct. 7, 2009

(65) Prior Publication Data
US 2010/0087504 A1    Apr. 8, 2010

Related U.S. Application Data

(60) Provisional application No. 61/103,507, filed on Oct. 7, 2008.

(51) Int. Cl.
*A01N 43/38* (2006.01)
*A61K 31/405* (2006.01)
*C07D 209/04* (2006.01)

(52) U.S. Cl.
USPC .......................................... 514/415; 548/511

(58) Field of Classification Search
USPC .......................................... 514/415; 548/511
See application file for complete search history.

(56) References Cited

U.S. PATENT DOCUMENTS

| 5,948,808 | A  | 9/1999  | Safe         |
| 7,232,843 | B2 | 6/2007  | Safe         |
| 7,304,171 | B2 | 12/2007 | Pei          |
| 2002/0115708 | A1 | 8/2002  | Safe         |
| 2006/0084694 | A1 | 4/2006  | Safe et al.  |

FOREIGN PATENT DOCUMENTS

| WO | WO 98/50357      |    | 11/1998 |
| WO | WO 2005016339 A1 | *  | 2/2005  |

OTHER PUBLICATIONS

Song et. al., Bioorganic and Medicinal Chemistry Letters, 2003, Pergamon, vol. 13, pp. 297-300.*
Hagmann et. al., Bioorganic and Medicinal Chemistry Letters, 2000, Pergamon, vol. 10, pp. 1975-1978.*
Davey et. al., Journal of Medicinal Chemistry, 2007, American Chemical Society, vol. 50, pp. 1146-1157.*
Zarkovic, Molecular Aspects of Medicine, 2003, Pergamon, vol. 24, pp. 293-303.*
Wenning et. al., The Lancet:Neurology, 2004, American Academy of Neurology, vol. 3, pp. 93-103.*
Wooten, Neurology, 2003, Lippincott Williams & Wilkins, vol. 60, pp. 360-362.*
Harrison et al. (1993) Tetrahedron Letters 34(52):8527-8530, "Synthesis of Cyclopent[b]indoles by Formal [3+2]-Addition of Indolylmethyl Cations to Alkenes".
Safe, S.H., et al. (1996) In: Estrogens, Progestins and Their Antagonists (E. Pavlik, ed.), Birkhouser, Boston. 73-97, "Dietary Indoles with Antiestrogenic Activity in Common Vegetables and Their Implications.".
Abdelrahim et al., (2006) Carcinogenesis, 27(4):717-728, "3,3'-Diindolylmethane (DIM) and its Derivatives Induce Apoptosis in Pancreatic Cancer Cells Through Endoplasmic Reticulum Stress-Dependent Upregulation of DR5".
Akgun et al. (1983) Journal of Heterocyclic Chemistry 20(5):1303-1305, "Reaktionen von elektronenreichen Heterocyclen mit Orthocarbonsaure-​Derivaten. I. Zum Reaktionsverhalten von acyclischen Orthoestern mit Indolen unter Saurekatalyse".
Alexander, I. et al. (1990) Mol. Endo. 4(6):821-828, "Progestin Regulation of Estrogen Receptor Messenger RNA in Human Breast Cancer Cells" abstract only.
Bergman (1972) Acta Chemica Scandinavica 26(3):970-974, "Synthesis of Some 3-Indolylvinylene Ketones".
Bergman et al. (1978) Tet. Lett. 42:4051-4054, "A novel synthesis of 2-amino- and 2- hydroxycarbazoles".
Bergman et al. (1989) Tetrahedron 45(17):5549-64, "Structure elucidation of some products obtained by acid-catalyzed condensation of indole with acetone".
Bergman et al., (1969) Acta Chemica Scandinavica 23(8):2578-2582, "Terpenoid N-heterocycles".
Berti et al., (1961) Gazzetta Chimica Italiana CA56:11541e 91:571, "Determination of the base strengths of some indole derivatives".
Brockman et al., (1998) Gastroenterology 115:1049-1055, "Activation of PPAR.gamma. leads to inhibition of anchorage independent growth of human colorectal cancer cells".
Bukin et al., (1987) Bioorganic Chemistry 13(4):539-545, "Ascorbingen and Its Derivatives as Depot-Forms of Ascorbic Acid".
Calabro et al., (2005) Journal of Vascular Research 42(6):509-516, "Inhibition of Tumor-Necrosis-Factor-α Induced Endothelial Cell Activation by a New Class of PPAR-γ Agonists : An in Vitro Study Showing Receptor-Independent Effects".
Chen, I., et al. (1995) Organohalogen Compounds 25:57-60, "Inhibition of TCDD-Induced Responses in B6C3F1 Mice and Hepa 1c1c7 Cells by Indole-3-Carbinol".
Chen et al. (1996) Biochem. Pharmacol. 51:1069-1076, "Indole-3-carbinol and diindolylmethane as aryl hydrocarbon (Ah) receptor agonists and antagonists in T47D human breast cancer cells".
Chen et al., (1998) Carcinogenesis 19:1631-1639, "Aryl hydrocarbon receptor-mediated antiestrogenic and antitumorigenic activity of diindolylmethane".
Chen et al., (2001) Gene 262:207-214, "Identification of estrogen-induced genes downregulated by AhR agonists in MCF-7 breast cancer cells using suppression subtractive hybridization".
Chintharlapalli et al., (2004) Cancer Research 64(17):5994-6001, "1,1-Bis(3'-indolyl)-1-(p-substitutedphenyl)methanes Induced Peroxisome Proliferator-Activated Receptor Gamma-Mediated Growth Inhibition, Transactivation, and Differentiation Markers in Colon Cancer Cells".

(Continued)

*Primary Examiner* — Sreeni Padmanabhan
*Assistant Examiner* — Sarah Pihonak
(74) *Attorney, Agent, or Firm* — Swanson & Bratschun, LLC

(57) ABSTRACT

Presented herein are diindolylmethane derivative compounds useful for the prevention and or treatment of neurological conditions, including neurological conditions related to neuroinflammation. One such neurological condition is Parkinson's disease.

5 Claims, 15 Drawing Sheets

(56) References Cited

OTHER PUBLICATIONS

Chintharlapalli et al., (2006) Molecular Cancer Therapeutics 5(5):1362-1370, "1,1-Bis(3'-indolyl)-1-(p-substituted phenyl)methanes Inhibit Colon Cancer Cell and Tumor Growth Through PPARgamma-Dependent and PPARgamma-Independent Pathways".

Chintharlapalli et al., (2007) Molecular Pharmacology 71(2):558-569, "1,1-bis(3'-indolyl)-1-(p-substitutedphenyl)methanes Inhibit Growth, Induced Apoptosis, and Decrease the Androgen Receptor in LNCaP Prostate Cancer Cells Through Peroxisome Proliferator-Activated Receptor Gamma-Independent Pathways".

Dashwood et al., (1989) Journal of Labelled Compounds and Radiopharmaceuticals 27(8):901-907, "The Synthesis of [3H]-Indole-3-Carbinol, A Natural Anti-Carcinogen From Cruciferous Vegetables".

Dehmer et al., (2004) Journal of Neurochemistry 88(2):494-501, "Protection by Pioglitazone in the MPTP Model of Parkinson's Disease Correlates With 1 Kappa B Alpha Induction and Block of NF Kappa B and iNOS Activation".

Denis et al. (1997) Tet. Lett. 38(49):8515-8518, "The reaction of nitrones with indoles. synthesis of asymmetrical diindolylalcanes".

Dmitrienko et al., (1980) Canadian Journal of Chemistry. 58(8):808-814, "The Bromination and Chlorination of 2,3-Dialkylindoles. Isolation of 3-Bromo- and 3-Chloro-2,3-dialkylindolenines and Acid Catalyzed Conversion to 3-Methoxyindolenines".

El Gihani et al., (1996) Synlett 9:871-872, "Scandium and Cooper Triflate-Catalysed Acylaminoalkylation and Friedel-Crafts Alkylation Reactions".

Elstner et al. (1998) Proc. Natl. Acad. Sci. USA 95:8806-8811, "Ligands for peroxisome proliferator-activated receptor gamma and retinoic acid receptor inhibit growth and induce apoptosis of human breast cancer cells in vitro and in BNX mice".

Foldeak et al., (Porszasz, Gibiszer-Porszasz, Foldeak, Matkovics)(1966) Acta physiologica 29(3):299, CA64:9670c and CA64:9670d, "Pharmacology of a new neuroplegic compound N,N'-di(piperidinomethyl)- 3,3'-diindolyl-methane".

Francis et al., (1980) Biomedical Mass Spectrometry 7(7):294-300, "Mass Spectrometric and Chromatographic Characteristics of Neutral and Acidic 5-Methoxyindoles and Some Related Compounds".

Garcia-Morales, P. et al. (1994) J. of Bio. Chem. 269(24):16896-16901, "Effect of Cadmium on Estrogen Receptor Levels and Estrogen-induced Responses in Human Breast Cancer Cells*".

Guilbaud, N. et al., (1990) Jour. of Cell. Phys. 145(1):162-172, "Effects of Differentiation-Inducing Agents on Maturation of Human MCF-7 Breast Cancer Cells".

Hanley et al., (1990) J. Chem. Soc., Perkin Trans.1(8):2273-2276, "Chemistry of Indole Glucosinolates: Intermediacy of Indol-3-ylmethyl Isothiocyanates in the Enzymic Hydrolysis of Indole Glucosinolates".

Hanley et al., (1990) Oppor. Biotransform, 6:44-46, "Indole Glucosinolates and Phytoalexins in Cruciferous Crops".

Hill et al., (1972) J.C.S. Perkin Trans 1(9/10):1210-1219, "Light-Induced Reactions of alpha-N-Alkylanilino-Ketones: Formation of Di-indolylmethanes".

Hong et al., (2008) Molecular Carcinogenesis 47(7):492-507, "1,1-bis(3'-indolyl)-1-(p-substituted phenyl)methanes Decrease Mitochondrial Membrane Potential and Induced Apoptosis in Endometrial and Other Cancer Cell Lines".

Jackson et al., (1987) J. Chem. Soc. Perkin Trans. 1(11):2543-2551, "Electrophilic Subsitution in Indoles".

Kassouf et al., (2006) Cancer Research 66(1):412-418, "Inhibtion of Bladder Tumor Growth by 1,1-bis(3'-indolyl)-1-(p-subsitutedphenyl) methanes: A New Class of Peroxisome Proliferator-Activated Receptor Gamma Agnosis".

Kiang and Mann (1953) Journal of Chemical Society, Abstracts 594. CAS, "The Action oj Acyl OyanideB on 2- and 1 : 2-Substituted IndoleB. Part 1".

Krichevskii et al., (1990) 26(5):622-624, "Synthesis of Azoxyindole Derivatives, Chemistry of Heterocyclic Compounds".

Leete, (1959) School of Chemistry, University of Minnesota, CA54:6684a, CA54:6684b, CA54:6684c and CA54:6684d, "3-Hydroxymethylindoles".

Lei et al., (2008) Carcinogenesis 29(6):1139-1147, "1,1-Bis(3'-indolyl)-1-(p-subsitutedphenyl)methanes Inhibit Colon Cancer Cell and Tumor Growth Through Activation of c-jun N-terminal Kinase".

Lerch et al., (1971) J. Org. Chem. 36(25):3861-3869, "Carbodiimide-Sulfoxide Reactions".

Liu, H. et al. (1994) J. Natl. Cancer Inst. 86(23):1758-1765, "Indolo[3,2-b]carbazole: a Dietary-Derived Factor That Exhibits Both Antiestrogenic and Estrogenic Activity".

Luna-Medina et al., (2005) Journal of Biological Chemistry 280(22):21453-21462, "Regulation of Inflammatory Response in Neural Cells In Vitro by Thiadiazolidinones Derivatives Through Peroxisome Proliferator-Activated Receptor Gamma Activation".

Magness et al., (2004) J. Immunol. 173(3):1561-1570, "In Vivo Pattern of Lipopolysaccharide and Anti-CD3-Induced NF-kappa B Activation Using a Novel Gene-Targeted Enhanced GFP Reporter Gene Mouse".

Maragakis et al. (Dec. 2006) Nature Clinical Practice, 2(12):679-689, "Mechanism of Disease: Astrocytes in neurodegenerative disease".

Mattocks, (1978) J.C.S. Perkin Trans. 1(8):896-905, "Pyrrolizidine Alkazloid Analogues".

McDougal and Safe (1998) Organohalogen Compounds 37:253-256, "Methyl-substituted diindolylmethanes as AhR-based antitumorigenic/antiestrogenic compounds".

McDougal et al. (2000) Cancer Letts., 151:169-179, "Inhibition of carcinogen-induced rat mammary tumor growth and other estrogen-dependent responses by symmetrical dihalo-substituted analogs of diindolylmethane".

McDougal et al., (2001) Cancer Res. 61:3902-3907, "Tamoxifen-induced antitumorigenic/antiestrogenic action synergized by a selective aryl hydrocarbon receptor modulator".

McDougal, A. et al. (1999) Chemical Abstracts 130(16) Abstract No. 204767t, "Methyl-substituted diindolylmethanes as AhR-based antitumorigenic/antiestrogenic compounds".

Michaud et al., (1999) J. Natl. Cancer Inst. 91:605-613, "Fruit and vegetable intake and incidence of bladder cancer in a male prospective cohort".

Mueller et al. (1998) Mol. Cell 1:465-470, "Terminal differentiation of human breast cancer through PPAR".

Mukhanov et al., (1984) Bioorganic Chemistry 10(4):544-559, "Ascorbigen and Its Derivatives".

Mukhanov et al., (1994) Khim. Farm. Zh. 28(7):6-10, "Neoascorbigen and Its Analogs: Synthesis and Study ".

Noland et al. (1961) Journal of Organic Chemistry 26:4263-9, "Cyclizative Condensations. IV. 3,3'-Alkylidenebisindoles from Methyl Ketones and Their Conversion to Indolo[2,3-b]carbazoles1".

Noland et al., (1967) Journal of Organic Chemistry 32(3):828-832, "Synthesis and Reactions of 5-Bromskatole and 5-Bromo-1,3-dimethylindole".

Noland et al., (1963) School of Chemistry, University of Minnesota, CA59:15247a "Nitration of Indoles. II. The Mononitration of Methylindoles1".

Noland et al., (1963) Organic Syntheses, 43:40, "Ethyl indole-2-carboxylate".

Pascual et al., (2005) Nature 437(7059):759-763, "A SUMOylation-Dependent Pathway Mediates Transrepression of Inflammatory Response Genes by PPAR-gamma".

PCT International Search Report mailed Jul. 31, 2002, in PCT/US01/42519.

Plikhtyak et al., (1991) Khim. Farm. Zh. 25(6):57-59, "Indole 3-Hydroxymethylation and Synthesis of Ascorbigens" in English.

Qin et al., (2004) Molecular Cancer Therapeutics 3(3):247-260, "A New Class of Peroxisome Proliferator-Activated Receptor gamma (PPARgamma) Agonists That Inhibit Growth of Breast Cancer Cells: 1,1-Bis(3'-indolyl)-1-(p-substituted phenyl)methanes".

Ramamoorthy et al. (1998) Organohalogen Compounds 37:321-324, "AhR-mediated antiestrogenicity of diindolylmethane and analogs in vivo and in vitro".

(56) References Cited

OTHER PUBLICATIONS

Rannug et al., (1991) Carcinogenesis12(11):2007-2015, "Use of Artificial Intelligence in Structure-Affinity Correlations of 2,3,7,8-Tetrachlorodibenzo-p-dioxin (TCDD) Receptor Ligand".

Saceda, M., et al., (1988) Mol. Endo. 2(12):1157-1162, "Regulation of the Estrogen Receptor in MCF-7 Cells by Estradiol".

Safe (1999) Endocrine Disrupters, Naz (ed.), CRC Press, Boca Raton, Florida, pp. 187-221, "2,3,7,8-Tetrachlorodibenzo-pdioxin (TCDD) and related environmental antiestrogens: characterization and mechanism of action".

Safe (2001) Toxicol. Lett. 120:1-7, "Molecular biology of the Ah receptor and its role in carcinogenesis".

Safe (2001) Vitam. Horm. 62:231-252, "Transcriptional activation of genes by 17 beta-estradiol through estrogen receptor-Sp1 interactions".

Safe et al., (1998) Toxicol. Lett. 102-103:343-7, "Ah receptor agonists as endocrine disruptors: antiestrogenic activity and mechanisms".

Sanderson et al., (2001) Toxicol Sci. 61(1):40-48, "2,3,7,8-Tetrachlorodibenzo-p-dioxin and diindolylmethanes differentially induce cytochrome P450 1A1, 1B1 and 19 in H295R human adrenocortical carcinoma cells".

Suda et al., (1994) Chemistry Letters 10:1915-1916, "A Novel Electrochemical Oxidation Reactions Utilizing Cyclodextrins. Anodic Oxidation of Indole-Cyclodextrin-Alcohol System".

Suh et al. (1999) Cancer Res. 59:5671-5673, "A new ligand for the peroxisome proliferator-activated receptor-PPAR, GW7845, inhibits rat mammary carcinogenesis".

Tjalkens et al., (2008) J. Neruosci. Res. 86(3):618-629, "The Peroxisome Proliferator-Activated Receptor-gamma Agonist 1,1-bis(3'-indolyl)-1-(p-trifluoromethylphenyl)methane Suppresses Manganese-Induced Production of Nitric Oxide in Astrocytes and Inhibits Apoptosis in Cocultured PC12 Cells".

Tontonoz et al. (1997) Proc. Natl. Acad. Sci. USA 94:237-241, "Terminal differentiation of human liposarcoma cells induced by ligands for peroxisome proliferator-activated receptor and the retinoid X receptor".

Toyota et al., (1992) Chem. Soc. Perkin Trans. 1(5):547-552, "Tandem Michael Addition[3,3]Sigmatropic Rearrangement Processes. Part 2. Construction of Cyclopropa[3,4]pyrrolo[3,2- e]indo1-4-one (CPI) Unit of Antitumor Antibiotic CC-1065".

Wormke et al., (2000) J. Steroid Biochem. Mol. Biol. 72(5):197-207, "Estrogen and aryl hydrocarbon receptor expression and crosstalk in human Ishikawa endometrial cancer cells".

Yamada et al., (1993) Heterocycles vol. 36, "A Synthesis Method of Indole-3-Methanamine and/or Gramine From Indole-3-Carboxaldehyde, and Its Application for the Synthesis of Brassinin, Its 4-Substituted Analogs, and 1,3,4,5-Tetrahydropyrrolo[4,3,2-de]quinoline".

International Search Report and Written Opinion prepared by the U.S. Patent and Trademark Office as International Searching Authority (ISA/US) for PCT International Patent Application No. PCT/US09/59896, mailed Feb. 23, 2010, 13 pages.

Guo et al. (2010) Cancer Chemother Pharmacol 66:141-150 "Peroxisome proliferator-activated receptor γ-dependent activity of indole ring-substituted 1,1-bis(3'-indolyl)-1-(p-biphenyl)methanes in cancer cells".

Inamoto et al. (2008) Mol Cancer Ther 7(12):3825-3833 "1,1-Bis(3'-indolyl)-1-(p-chlorophenyl)methane activates the orphan nuclear receptor Nurr1 and inhibits bladder cancer growth".

Li et al. (2012) Biochemical Pharmacology 83:1445-1455 "Structure-dependent activation of NR4A2 (Nurr1) by 1,1-bis(3'-indolyl)-1-(aromatic)methane analogs in pancreatic cancer cells".

\* cited by examiner

| Differential Expression of Representative NF-kB-regulated genes by cDIM's | | | MPTP/TNF/IFN | | MPTP/TNFα/IFNγ | | |
|---|---|---|---|---|---|---|---|
| Accession # | Gene Symbol | Gene Name | MPTP/TNF/IFN | DIM-C-pPhtBu | DIM-C-pPhOCH₃ | Rosi | DMSO |
| NM_011333 | Ccl2 | Chemokine (C-C motif) ligand 2 | 15.4 | -1.1 | 2.2 | 1.7 | 7.5 |
| NM_010234 | Fos | FBJ osteosarcoma oncogene | -1.5 | -3.3 | -3.1 | -8.2 | -7.4 |
| NM_010493 | Icam1 | Intercellular adhesion molecule 1 | 8.8 | 1.3 | 2.2 | 1.1 | 4.7 |
| NM_010548 | Il10 | Interleukin 10 | -2.3 | -1.5 | -1.2 | -1.4 | -2.4 |
| NM_008361 | Il1b | Interleukin 1 beta | -2.7 | -1.8 | -1.6 | -1.0 | -2.3 |
| NM_008390 | Irak1 | Interleukin-1 receptor-associated kinase 1 | 1.6 | -1.0 | -3.4 | -3.8 | -2.5 |
| NM_011163 | Eif2ak2 | Eukaryotic translation initiation factor 2-alpha kinase 2 | 2.7 | -1.3 | 1.2 | 1.1 | 2.4 |
| NM_009068 | Ripk1 | Receptor (TNFRSF)-interacting serine-threonine kinase 1 | 2.8 | -1.1 | 1.2 | 1.6 | 2.4 |
| NM_009283 | Stat1 | Signal transducer and activator of transcription 1 | 5.9 | 2.0 | 3.8 | 3.1 | 5.3 |
| NM_126166 | Tlr3 | Toll-like receptor 3 | 4.8 | 1.5 | -1.3 | -1.3 | 2.2 |
| NM_011609 | Tnfrsf1a | Tumor necrosis factor receptor superfamily, member 1a | 3.4 | -1.3 | 1.6 | 1.5 | 3.1 |
| NM_011611 | Cd40 | CD40 antigen | 14.3 | 1.2 | 1.5 | 1.5 | 8.3 |
| NM_009425 | Tnfsf10 | Tumor necrosis factor (ligand) superfamily, member 10 | 51.2 | 4.4 | 6.9 | 5.1 | 34.6 |

Expression reported as fold-change relative to saline-treated (control) astrocytes. Bold type indicates significance ($p < 0.05$).

Figure 11A

USE OF DIINDOLYLMETHANE (DIM) COMPOUNDS AND DERIVATIVES AS NEUROPROTECTIVE AGENTS

STATEMENT OF RIGHTS TO INVENTIONS MADE UNDER FEDERALLY SPONSORED RESEARCH

This work was supported by the government, in part, by grants from the National Institutes of Health and National Institute of Neurological Disorders and Stroke (NS055632), National Institutes of Health/National Institute of Environmental Health Sciences, Grant No. ES012941, and National Institutes of Health, Grant #R01 ES012941. Thus, the government has certain rights to this invention.

RELATED APPLICATIONS

This application claims priority from U.S. Provisional Patent Application Ser. No. 61/103,507, filed on Oct. 7, 2008, entitled "Suppression of 1-methyl-4-phenyl-1,2,3,6-tetrahydropyridine-induced nitric oxide synthase 2 expression in astrocytes by a novel diindolymethane analog protects striatal neurons against apoptosis," which is hereby incorporated by reference in its entirety. Each of the applications and patents cited herein are hereby expressly incorporated herein by reference and may be employed in the practice of the invention.

BACKGROUND

Incorporated by reference herein in its entirety is the Sequence Listing submitted on Nov. 17, 2009, entitled "sequence listing 11.13.2009.txt", size of 2 kilobytes, created Nov. 13, 2009.

Parkinson's disease (PD) is a severely debilitating movement disorder resulting from progressive degeneration of dopaminergic neurons within the substantia nigra pars compacta of the midbrain. Unfortunately, pharmacologic treatment for PD has not progressed beyond the use of dopamine mimetics, such as L-dopa, that only transiently alleviate motor symptoms. Furthermore, chronic use of L-dopa is associated with its own array of resultant pathologies such as dyskinesia (Lang and Lozano, 1998), cardiac arrhythmia and ischemic injury, and cerebral vascular dysfunction (Ben-Shlomo and Marmot, 1995). Ultimately, individuals suffering from PD will progress to the end stage of the disease, which is characterized by significant gait abnormalities and frequent falls, as well as a deficit in non-motor functions resulting in dementia, psychosis, and other autonomic disturbances (Djaldetti et al., 2004).

Over 1.5 million individuals are currently diagnosed with PD, with an additional 50,000 expected diagnoses annually, making this disease the second most prevalent neurological disorder behind Alzheimer's disease (Teismann and Schulz, 2004). While the reason for selective neuronal loss in PD remains poorly explained, chronic inflammation and activation of glial cells has been consistently observed in PD models as well as following postmortem evaluation, and provide a realistic target for slowing the progression of neuronal injury.

Currently, a precise etiology explaining PD remains to be discovered but recent research has revealed features of the disease that represent realistic targets for neuroprotective chemotherapeutic intervention that could mitigate the progressive loss of dopaminergic neurons. Among these observations are the presence of chronic inflammation and sustained expression of inducible nitric oxide (NOS2), accompanied by activation of the surrounding astrocytes and microglia.

Astrocytes have diverse and critical functions in the CNS that include providing energetic, antioxidant, and other trophic support essential for the survival and function of neurons. However, many neurological disease states, including PD, Alzheimer's disease, and ischemic injury are typically accompanied by varying degrees of astrocyte activation, or astrogliosis. While the exact cause of astrogliosis in PD is unknown, several reports have suggested that the activation of astrocytes is due to secretion of inflammatory cytokines, such TNF-α and IFN-γ, by the surrounding microglial cells. While some degree of activation is likely beneficial, reactive astrogliosis results in neuronal injury.

Astrogliosis results in increased production of various neurotoxic inflammatory mediators, including nitric oxide (NO), which contributes to progressive loss of nigro-striatal neurons. Supporting a deleterious role for excessive NO production in PD are postmortem observations of increased NOS2 expression in patients diagnosed with PD, as well as reports that deletion of the Nos2 gene in mice confers protection against MPTP-mediated neurotoxicity. Expression of NOS2 in diverse cell types is highly dependent upon the NF-κB signaling pathway and we previously demonstrated a requirement for NF-κB in the expression of NOS2 in activated astrocytes following stimulation with inflammatory cytokines and manganese. Multiple signaling pathways activate NF-κB through the IκB kinase (IKK) complex, leading to phosphorylation and degradation of the inhibitory IκB subunit and nuclear translocation of the transcriptionally active p65 subunit. Ensuing induction of Nos2 then typically requires binding of p65 to enhancer sequences on the Nos2 promoter and removal of constitutively bound nuclear co-repressor proteins such as NCoR2 by the nuclear proteosome.

Suppressing neuroinflammation has emerged as a potential strategy for treating disorders such as PD. Specifically, modulation of nuclear orphan receptors has been examined as a possible approach for suppressing inflammatory gene expression in astrocytes using traditional thiazoladinedione (TZD) ligands of PPAR-γ. The TZD ligand rosaglitazone (5-((4-(2-(methyl-2-pyridinylamino)ethoxy)phenyl)methyl)-2,4-thiazolidinedione) appears to antagonize NF-κB by stabilizing NCoR2 at the proximal p65 enhancer element in RAW macrophages. However, another drug in this series, pioglitazone, confers only partial neuroprotection in the MPTP model of Parkinson's disease, preserving dopaminergic cell bodies in the substantia nigra but not dopaminergic fibers in the striatum. However, there remains a pressing need for better compounds and strategies to treat neurodegenerative conditions that have a neuroinflammatory component in their progression, including Parkinson's disease.

U.S. Pat. No. 5,948,808 discloses use of indole-3-carbinol, diindolylmethane and substituted analogs as antiestrogenic compounds suitable for treating estrogen-dependent tumors. U.S. Pat. No. 7,232,843 discloses diindolylmethane, ring substituted diindolylmethane, and C-substituted diindolylmethanes and analogs thereof as antiestrogenic and antitumoric agents. The disclosures of these U.S. patents are specifically incorporated by reference herein.

The present invention is directed toward overcoming one or more of the problems discussed above.

SUMMARY

In one aspect, the present invention provides a method for treating a neurological condition in a subject, comprising administering to the subject a therapeutically effective amount of a composition comprising a compound of Formula (I)

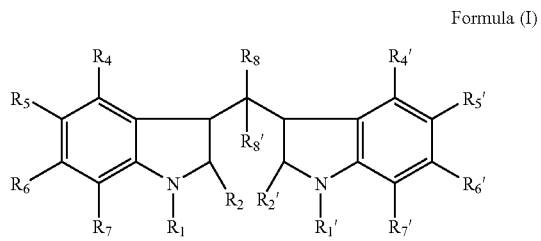

Formula (I)

wherein $R_1$, $R_2$, $R_4$, $R_5$, $R_6$, $R_7$, $R_1'$, $R_2'$, $R_4'$, $R_5'$, $R_6'$, and $R_7'$ are independently selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring; wherein $R_8$ and $R_8'$ are independently selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring; or a pharmaceutically acceptable salt, stereoisomer, or prodrug thereof.

In another aspect, compounds of Formula (I) include compounds wherein $R_1$, $R_2$, $R_1'$, $R_2'$, are independently selected from the group consisting of hydrogen and methyl; $R_4$, $R_6$, $R_7$, $R_4'$, $R_6'$, and $R_7'$ are each H; and one of $R_8$ and $R_8'$ is H and the other is selected from a linear $C_1$-$C_{10}$ alkyl, a branched $C_1$-$C_{10}$ alkyl, a $C_1$-$C_{10}$ cycloalkyl, a $C_1$-$C_{10}$ haloalkyl, a $C_1$-$C_{10}$ heteroalkyl, and an aryl, substituted aryl, heteroaryl and substituted heteroaryl, each having 5 or 6 members in the aromatic ring.

In another aspect, compounds of Formula (I) include compounds wherein one of $R_8$ and $R_8'$ is H and the other is a substituted or unsubstituted phenyl of Formula (III)

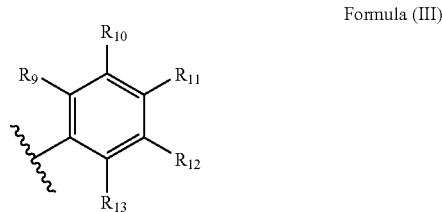

Formula (III)

wherein $R_9$, $R_{10}$, $R_{11}$, $R_{12}$ and $R_{13}$ are independently selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring.

In another aspect, compounds of Formula (I) include compounds wherein one of $R_8$ and $R_8'$ is H and the other is selected from the group consisting of unsubstituted or singly or multiply substituted methyl, ethyl, propyl, isopropyl, butyl, tert-butyl, chloromethyl, dichloromethyl, trichloromethyl, fluoromethyl, difluoromethyl, trifluoromethyl, phenyl, 2-methylphenyl, 3-methylphenyl, 4-methylphenyl 2-ethylphenyl, 3-ethylphenyl, 4-ethylphenyl, 2-isopropylphenyl, 3-isopropylphenyl, 4-isopropylphenyl, 2-propylphenyl, 3-propylphenyl, 4-propylphenyl, 2-sec-butylphenyl, 3-sec-butylphenyl, 4-sec-butylphenyl, 2-t-butylphenyl, 4-t-butylphenyl and 4-t-butylphenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl, 4-bromo-2-methylphenyl, phenol, naphthyl, and biphenyl.

In another aspect of the invention, compounds of Formula (I) are selected from the group consisting of 1-bis(3'-indolyl)-1-(p-trifluoromethylphenyl)methane, 1,1-bis(3'-indolyl) -1-(p-t-butylphenyl)methane, 1,1-bis(3'-indolyl)-1-(p-chlorophenyl)methane, 1,1-bis(3'-indolyl) -1-(phenyl)methane, 1-bis(3'-indolyl)-1-(naphthyl)methane, 3,3'-(biphenyl-4-yl-methylene)bis(1H-indole), 1,1-bis(3'-indolyl)-1-(p-hydroxyphenyl)methane, 1,1-bis(3'-indolyl)-1-(p-methylphenyl)methane, and 1,1-bis(3'-indolyl)-1-(p-methoxyphenyl)methane.

BRIEF DESCRIPTION OF THE FIGURES

The following Detailed Description of the Invention, given by way of Examples, but not intended to limit the invention to specific embodiments described, may be understood in conjunction with the accompanying figures, in which:

FIG. 7(A) shows semi-quantitative real-time RT-PCR demonstrating dose-responsive suppression of Nos2 mRNA by concentrations of DIM-C-pPhOCH$_3$ ranging from 0.1 to 3 μM in astrocytes challenged with MPTP, TNF-α, and IFN-γ. FIG. 7(B) shows semi-quantitative real-time PCR demonstrating equivalent suppression of Nos2 mRNA by either DIM-C-pPhOCH$_3$ or rosiglitazone in astrocytes challenged with MPTP, TNF-α, and IFN-γ. FIG. 7(C) shows that immunoblotting demonstrates suppression of NOS2 protein expression by either DIM-C-pPhOCH$_3$ or rosiglitazone in astrocytes exposed to MPTP and TNF-α/IFN-γ. FIG. 7(D) shows that treatment with DIM-C-pPhOCH$_3$ or the NOS2 inhibitor, AMT, prevents protein nitration in primary astrocytes induced by MPTP and TNF-α/IFN-γ. Differing letters denote statistical significance (p<0.05).

FIG. 8(A) shows transgenic astrocytes expressing an NF-kB-GFP reporter construct were exposed to MPTP and TNF-α/IFN-γ in the absence or presence of 1 uM DIM-C-pPhOCH$_3$ or vehicle control (DMSO) showing blocked activation. FIG. 8(B) demonstrates that quantitative analysis of GFP fluorescence indicates that DIM-C-pPhOCH$_3$ completely abrogated MPTP- and cytokine-induced activation of NF-kB. Differing letters denote statistical significance (p<0.05).

FIG. 10(A) shows primary cultured astrocytes plated on permeable transwell inserts were treated with MPTP and TNF/IFN in the presence or absence of DIM-C-pPhOCH$_3$ (DIM5, 1 uM) or vehicle (DMSO) for 24 hrs, washed, and then incubated with primary striatal neurons cultured on glass cover slips for 6 hrs. Annexin IV binding was assessed in neurons by live-cell fluorescence imaging as a measure of apoptotic cell death (red fluorescence). MPTP and cytokine (CK) treatment increased Annexin IV binding that was inhibited by DIM-C-pPhOCH$_3$. FIG. 10(B) shows that quantitative determination of Annexin IV fluorescence indicates that DIM-C-pPhOCH$_3$ significantly reduced activation of astrocytes and subsequent neuronal apoptosis. Differing letters denote statistical significance (p<0.05).

FIG. 11 shows that DIM-C-pPhOCH$_3$ suppresses activation of a broad array of NF-kB-regulated genes in primary astrocytes. Expression of inflammatory genes in astrocytes is largely regulated through the NF-kB signaling pathway. Primary cultured astrocytes were treated with MPTP and TNF/IFN in the presence or absence DIM-C-pPhOCH$_3$ (DIM5, 1 uM), DIM-C-pPhtBu (DIM4), rosiglitazone (Ro, 10 uM), or vehicle (DMSO) and subjected to qPCR array analysis of NF-kB-regulated transcripts (Superarray Biosciences). FIG. 11(A) shows representative NF-kB-regulated genes depicted in tabular format, indicating that both DIM-C-pPhtBu and DIM-C-pPhOCH$_3$ suppressed neuroinflammatory gene expression of such transcripts as TNF Receptor, Toll Receptor, and Interleukin 1beta.

FIG. 12(A) shows that control animals did not display activation of astrocytes or expression of either NOS2 or NF-kB at significant levels. FIG. 12(B) shows that MPTP treatment induced marker hypertrophic activation of astrocytes that expressed both NOS2 and NF-kB/GFP. This activated glial phenotype was inhibited by treatment with DIM-C-pPhtBu.

DETAILED DESCRIPTION

Figure 1:
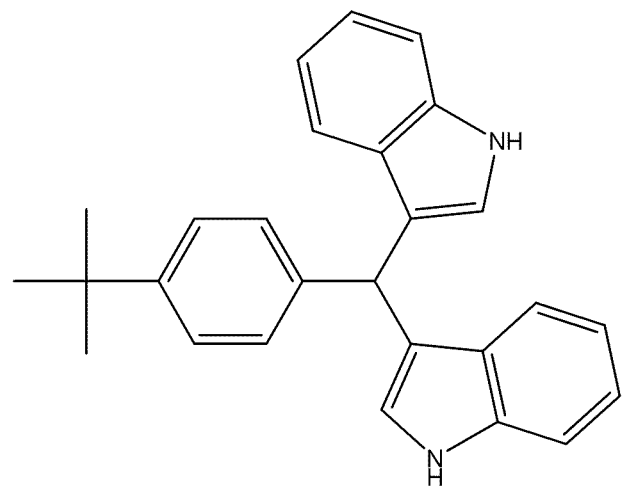
FIG. 1 shows the chemical structure of 1,1-bis(3'-indolyl)-1-(p-t-butylphenyl)methane (DIM-C-pPhtBu) and 1,1-bis(3'-indolyl)-1-(p-methoxyphenyl)methane (DIM-C-pPhOCH$_3$).
Figure 1:
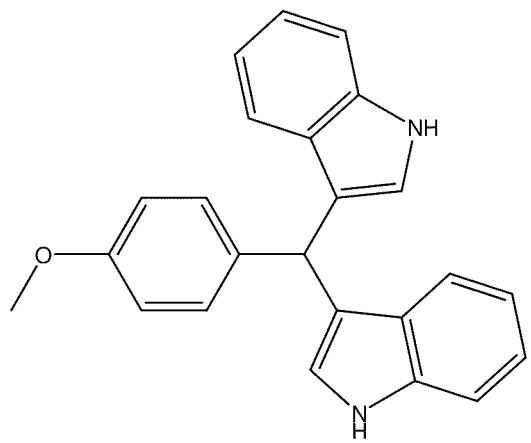

The present invention demonstrates that compounds of Formula (I)

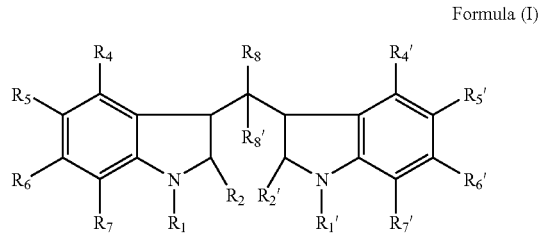

Formula (I)

or a pharmaceutically acceptable salt, stereoisomer, or prodrug thereof, are useful in the prevention and treatment of neurological conditions, including neurological disease, neurological degeneration, neuroinflammation, and neuroinflammatory injury related to neurodegenerative and neurological diseases. Such conditions include neurological conditions related to inflammation of glial cells, including inflammatory activation of astrocytes and microglial cells. Neurodegenerative and neurological diseases to prevent and/or treat include Parkinson's disease, Dementia with Lewy Bodies (Lewy Body disease), Multiple System Atrophy, Alzheimer's disease, Vascular Dementia, Huntington's disease, Amyotrophic Lateral Sclerosis (ALS, Lou Gehrig's Disease, Maladie de Charcot), Multiple Sclerosis, neurodegeneration related to stroke, neurodegeneration related to HIV-1 infection, neurodegeneration related to Spinocerebellar Ataxia and Friedrich's Ataxia, neurodegeneration related to Hemiballism (Hemiballismus).

A compound of Formula (I) is variously referred to herein as a diindolylmethane ("DIM"), a DIM derivative, a DIM analog, and/or a C-substituted DIM.

In one embodiment, provided is a compound having the structure

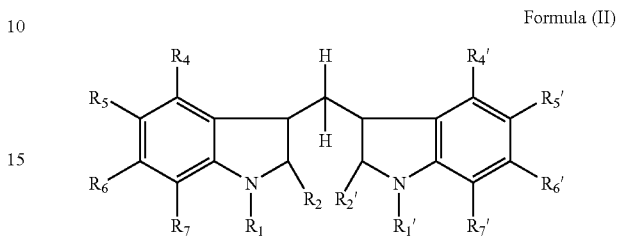

Formula (II)

wherein $R_1$, $R_2$, $R_4$, $R_5$, $R_6$, $R_7$, $R_1'$, $R_2'$, $R_4'$, $R_5'$, $R_6'$, and $R_7'$, are independently selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring; or a pharmaceutically acceptable salt, stereoisomer, or prodrug thereof, for the prevention and treatment of neurological conditions, including neurological disease, neurological degeneration, neuroinflammation, and neuroinflammatory injury related to neurodegenerative and neurological diseases. Such conditions include neurological conditions related to inflammation of glial cells, including inflammatory activation of astrocytes and microglial cells. Neurodegenerative and neurological diseases to prevent and/or treat include Parkinson's disease, Dementia with Lewy Bodies (Lewy Body disease), Multiple System Atrophy, Alzheimer's disease, Vascular Dementia, Huntington's disease, Amyotrophic Lateral Sclerosis (ALS, Lou Gehrig's Disease, Maladie de Charcot), Multiple Sclerosis, neurodegeneration related to stroke, neurodegeneration related to HIV-1 infection, neurodegeneration related to Spinocerebellar Ataxia and Friedrich's Ataxia, neurodegeneration related to Hemiballism (Hemiballismus).

In one embodiment, for compounds of Formula (II), $R_2$, $R_4$, $R_5$, $R_6$, $R_7$, $R_1'$, $R_2'$, $R_4'$, $R_5'$, $R_6'$, and $R_7'$ are each independently H. In one embodiment, for compounds of Formula (II), at least one of $R_1$, $R_2$, $R_4$, $R_5$, $R_6$, $R_7$, $R_1'$, $R_2'$, $R_4'$, $R_5'$, $R_6'$, and $R_7'$ is not H.

In one embodiment, $R_1$, $R_2$, $R_4$, $R_6$, $R_7$, $R_1'$, $R_2'$, $R_4'$, $R_6'$, and $R_7'$ are hydrogen, $R_5$ and $R_5'$ are a halogen selected from the group consisting of chlorine, bromine and fluorine. Accordingly, preferred DIM derivatives include 5,5'-dichloro-diindolylmethane, 5,5'-dibromo-diindolylmethane, and 5,5'-difluoro-diindolylmethane.

Additional embodiments of DIM derivatives include compounds wherein $R_1$, $R_2$, $R_4$, $R_6$, $R_7$, $R_1'$, $R_2'$, $R_4'$, $R_6'$, and $R_7'$ are hydrogen, $R_5$ and $R_5'$ are an alkyl or alkoxyl having from one to ten carbons, and most preferably one to five carbons. These include, but are not limited to 5,5'-dimethyl-diindolylmethane, 5,5'-diethyl-diindolylmethane, 5,5'-dipropyl-diindolylmethane, 5,5'-dibutyl-diindolylmethane and 5,5'-dipentyl-diindolylmethane. These also include, but are not limited to, 5,5'-dimethoxy-diindolylmethane, 5,5'-diethoxy-diindolylmethane, 5,5'-dipropyloxy-diindolylmethane, 5,5'-dibutyloxy-diindolylmethane, and 5,5'-diamyloxy-diindolylmethane.

Additional embodiments of DIM derivatives include compounds wherein $R_2$, $R_4$, $R_5$, $R_6$, $R_7$, $R_2'$, $R_4'$, $R_5'$, $R_6'$, and $R_7'$ are hydrogen, $R_1$ and $R_1'$ are an alkyl or alkoxyl having from one to ten carbons, and most preferably one to five carbons. Such useful derivatives include, but are not limited to, N,N'-dimethyl-diindolylmethane, N,N'-diethyl-diindolylmethane, N,N'-dipropyl-diindolylmethane, N,N'-dibutyl-diindolylmethane, and N,N'-dipentyl-diindolylmethane.

In yet another embodiment, $R_1$, $R_4$, $R_5$, $R_6$, $R_7$, $R_1'$, $R_4'$, $R_5'$, $R_6'$, and $R_7'$ are hydrogen, and $R_2$ and $R_2'$ are alkyl of one to ten carbons, and most preferably one to about five carbons. Such compounds include, but are not limited to, 2,2'-dimethyl-diindolylmethane, 2,2'-diethyl-diindolylmethane, 2,2'-dipropyl-diindolylmethane, 2,2'-dibutyl-diindolylmethane, and 2,2'-dipentyl-diindolylmethane.

In another embodiment, $R_1$, $R_2$, $R_4$, $R_6$, $R_7$, $R_1'$, $R_2'$, $R_4'$, $R_6'$, and $R_7'$ are hydrogen, and $R_5$ and $R_5'$ are nitro.

Also provided in the present invention is a compound selected from the group consisting of 5,5'-dichloro-diindolylmethane; 5,5'-dibromo-diindolylmethane; 5,5'-difluoro-diindolylmethane; 5,5'-dimethyl-diindolylmethane; 5,5'-diethyl-diindolylmethane; 5,5'-dipropyl-diindolylmethane; 5,5'-dibutyl-diindolylmethane; 5,5'-dipentyl-diindolylmethane; 5,5'-dimethoxy-diindolylmethane; 5,5'-diethoxy-diindolylmethane; 5,5'-dipropyloxy-diindolylmethane; 5,5'-dibutyloxy-diindolylmethane; 5,5'-diamyloxy-diindolylmethane; N,N'-dimethyl-diindolylmethane; N,N'-diethyl-diindolylmethane; N,N'-dipropyl-diindolylmethane; N,N'-dibutyl-diindolylmethane; N,N'-dipentyl-diindolylmethane; 2,2'-dimethyl-diindolymethane; 2,2'-diethyl-diindolylmethane; 2,2'-dipropyl-diindolylmethane; 2,2'-dibutyl-diindolylmethane and 2,2'-dipentyl-diindolylmethane.

In one embodiment of the invention, compounds include DIM compounds with modifications at the bridge carbon ("C-substituted DIMs"). These compounds can be symmetrical or asymmetrical, depending on whether a single indole precursor is used in the synthesis (leading to a symmetrical C-substituted DIM, or if two different indole precursors were used (leading to an asymmetrical C-substituted DIM).

Accordingly, in one embodiment, provided is a compound having the structure

Formula (I)

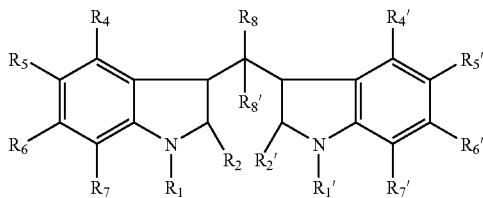

according to Formula (I) wherein $R_1$, $R_2$, $R_4$, $R_5$, $R_6$, $R_7$, $R_1'$, $R_2'$, $R_4'$, $R_5'$, $R_6'$, and $R_7'$ are independently selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring; wherein the halogen is selected from the group consisting of chlorine, bromine, and fluorine; and wherein $R_8$ and $R_8'$ are independently selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring; or a pharmaceutically acceptable salt, stereoisomer, or prodrug thereof.

Compounds of Formula (I), or a pharmaceutically acceptable salt, stereoisomer, or prodrug thereof, are useful for the prevention and treatment of neurological conditions, including neurological disease, neurological degeneration, neuroinflammation, and neuroinflammatory injury related to neurodegenerative and neurological diseases. Such conditions include neurological conditions related to inflammation of glial cells, including inflammatory activation of astrocytes and microglial cells. Neurodegenerative and neurological diseases to prevent and/or treat include Parkinson's disease, Dementia with Lewy Bodies (Lewy Body disease), Multiple System Atrophy, Alzheimer's disease, Vascular Dementia, Huntington's disease, Amyotrophic Lateral Sclerosis (ALS, Lou Gehrig's Disease, Maladie de Charcot), Multiple Sclerosis, neurodegeneration related to stroke, neurodegeneration related to HIV-1 infection, neurodegeneration related to Spinocerebellar Ataxia and Friedrich's Ataxia, neurodegeneration related to Hemiballism (Hemiballismus).

In a further aspect of the invention, suitable identities for $R_1$, $R_2$, $R_1'$, $R_2'$, are independently selected from the group consisting of hydrogen and methyl; $R_4$, $R_6$, $R_7$, $R_4'$, $R_6'$, and $R_7'$ are each H; and one of $R_8$ and $R_8'$ is H and the other is selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, and $C_1$-$C_{10}$ heteroalkyl.

In a further aspect of the invention, suitable identities for $R_1$, $R_2$, $R_1'$, $R_2'$, are independently selected from the group consisting of hydrogen and methyl; $R_4$, $R_6$, $R_7$, $R_4'$, $R_6'$, and $R_7'$ are each H; and one of $R_8$ and $R_8'$ is H and the other is selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring.

In one embodiment, one of $R_8$ and $R_8'$ is H and the other is a substituted or unsubstituted phenyl of Formula (III)

Formula (III)

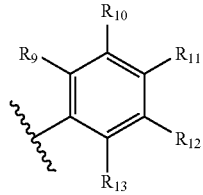

wherein $R_9$, $R_{10}$, $R_{11}$, $R_{12}$ and $R_{13}$ are independently selected from the group consisting of hydrogen, halogen, $C_1$-$C_{10}$ linear alkyl, $C_1$-$C_{10}$ branched alkyl, $C_1$-$C_{10}$ substituted alkyl, $C_1$-$C_{10}$ haloalkyl, $C_1$-$C_{10}$ carboxyl, hydroxy, $C_1$-$C_{10}$ hydroxyalkyl, $C_1$-$C_{10}$ alkoxy, $C_1$-$C_{10}$ aminoalkyl, $C_1$-$C_{10}$ heteroalkyl, and aryl, substituted aryl, heteroaryl and substituted heteroaryl, each having 5 or 6 members in the aromatic ring.

In a further aspect of the invention, one of $R_8$ and $R_8'$ is H and the other is selected from the group consisting of unsubstituted or singly or multiply substituted cyclopentyl, cyclohexyl, naphthyl, thiophenyl, benzothiophenyl, furyl, benzofuranyl, benzodioxolanyl, indolyl, indanyl, benzodioxanyl or pyridyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-10}$ alkyl group.

In a further aspect of the invention, one of $R_8$ and $R_8'$ is H and the other is selected from the group consisting of methyl, ethyl, propyl, isopropyl, butyl, tert-butyl, chloromethyl, dichloromethyl, trichloromethyl, fluoromethyl, difluoromethyl, trifluoromethyl, phenyl, 2-methylphenyl, 3-methylphenyl, 4-methylphenyl 2-ethylphenyl, 3-ethylphenyl, 4-ethylphenyl, 2-isopropylphenyl, 3-isopropylphenyl, 4-isopropylphenyl, 2-propylphenyl, 3-propylphenyl, 4-propylphenyl, 2-sec-butylphenyl, 3-sec-butylphenyl, 4-sec-butylphenyl, 2-t-butylphenyl, 4-t-butylphenyl and 4-t-butylphenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl, 4-bromo-2-methylphenyl, phenol, naphthyl, and biphenyl.

In one embodiment, at least one of $R_8$ and $R_8'$ are not hydrogen (if both $R_8$ and $R_8'$ are hydrogen, the compound is a DIM).

Suitable compounds of Formula (I) include where $R_1$, $R_2$, $R_1'$, and $R_2'$ are each individually hydrogen or methyl; $R_4$, $R_5$, $R_6$, $R_7$, $R_4'$, $R_5'$, $R_6'$, and $R_7'$ are each hydrogen; and $R_8$ and $R_8'$ are each individually hydrogen, methyl, $C_6H_5$, $C_6H_5Cl$, $C_6H_4OH$, $C_6H_4CH_3$, $C_6H_4CF_3$, $C_{10}H_7$, $C_6H_4C_6H_5$, or $C_6H_4OCH_3$.

Suitable compounds of Formula (I) include 1,1-bis(3'-indolyl)-1-(p-t-butylphenyl)methane (DIM-C-pPhtBu)

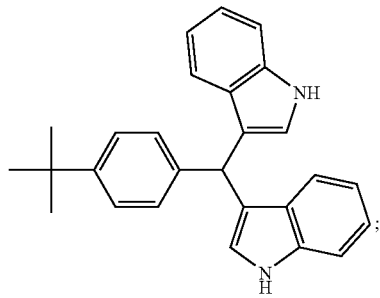 [SMILES: CC(C)(C)c1ccc(C(c2c[nH]c3ccccc23)c2c[nH]c3ccccc23)cc1]

1,1-bis(3'-indolyl)-1-(p-trifluoromethylphenyl)methane

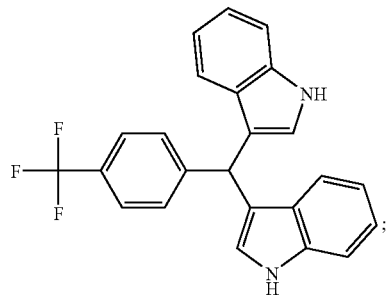 [SMILES: FC(F)(F)c1ccc(C(c2c[nH]c3ccccc23)c2c[nH]c3ccccc23)cc1]

1,1-bis(3'-indolyl)-1-(p-methoxyphenyl)methane (DIM-C-pPhOCH$_3$)

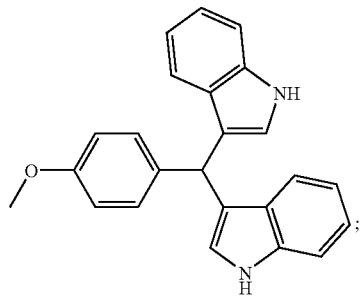 [SMILES: COc1ccc(C(c2c[nH]c3ccccc23)c2c[nH]c3ccccc23)cc1]

1,1-bis(3'-indolyl)-1-(p-chlorophenyl)methane

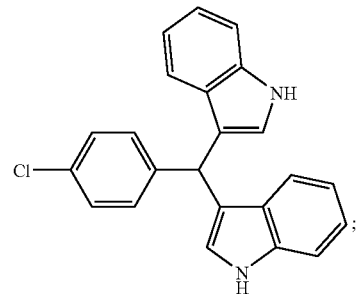 [SMILES: Clc1ccc(C(c2c[nH]c3ccccc23)c2c[nH]c3ccccc23)cc1]

1,1-bis(3'-indolyl)-1-(phenyl)methane

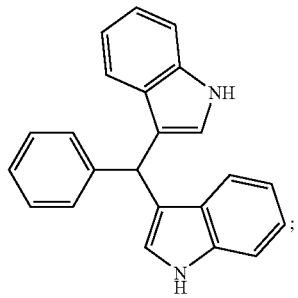 [SMILES: c1ccc(C(c2c[nH]c3ccccc23)c2c[nH]c3ccccc23)cc1]

1,1-bis(3'-indolyl)-1-(naphthyl)methane

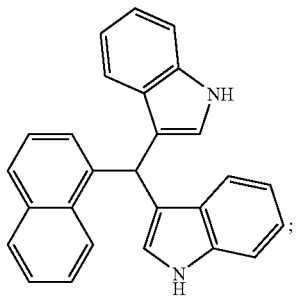 [SMILES: c1ccc2c(C(c3c[nH]c4ccccc34)c3c[nH]c4ccccc34)cccc2c1]

3,3'-(biphenyl-4-ylmethylene)bis(1H-indole)

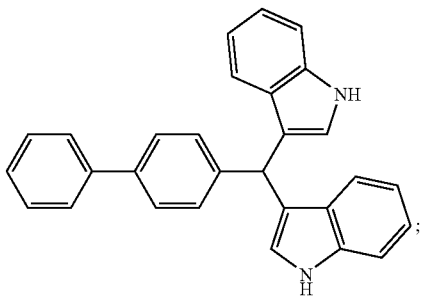 [SMILES: c1ccc(-c2ccc(C(c3c[nH]c4ccccc34)c3c[nH]c4ccccc34)cc2)cc1]

1,1-bis(3'-indolyl)-1-(p-hydroxyphenyl)methane

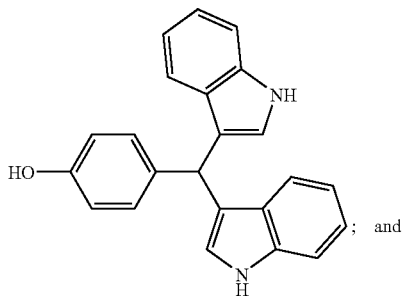 [SMILES: Oc1ccc(C(c2c[nH]c3ccccc23)c2c[nH]c3ccccc23)cc1]

; and 1,1-bis(3'-indolyl)-1-(p-methylphenyl)methane

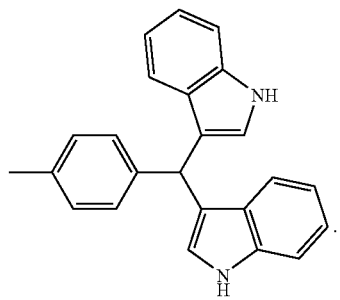 [SMILES: Cc1ccc(C(c2c[nH]c3ccccc23)c2c[nH]c3ccccc23)cc1]

Depending on the nature of the two indole subunits, and of $R_8$ and $R_8'$, it is possible for the bridging carbon atom to be a chiral center (a carbon atom with four different substituents attached). If a chiral center exists, then the resulting C-substituted DIM would consist of two mirror image enantiomers, each of which is optically active. Resolution of the mixture using a chiral chromatography column or other means would result in the isolation of purified or pure enantiomer products. The different enantiomers may prove to have different biological activities. Such compounds can exist in various isomeric forms, including configurational, geometric and conformational isomers, as well as existing in various tautomeric forms, particularly those that differ in the point of attachment of a hydrogen atom. As used herein, the term "isomer" is intended to encompass all isomeric forms of a compound including tautomeric forms of the compound.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood that isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

It should be noted that if there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of the described compound.

The synthesis of the substituted indole-3-carbinol derivatives from the commercially-available substituted indoles is a convenient method for preparation of these compounds. The substituted DIM analogs can also be prepared by condensation of formaldehyde with substituted indoles; however, a disadvantage of the latter reaction is the formation of by-products which will complicate purification of the desired substituted DIM. The compounds of the present invention can be synthesized by dimethylformamide condensation of a suitable substituted indole to form a substituted indole-3-carboxaldehyde. Suitable substituted indoles include those indoles having substituents at $R_1$, $R_2$, $R_4$, $R_5$, $R_6$ and $R_7$ positions. These include, but are not limited to 5-methoxy, 5-chloro, 5-bromo, 5-fluoro, 5-methyl, 5-nitro, N-methyl, and 2-methyl indoles. The substituted indole 3-aldehyde product is treated with a suitable alcohol such a methanol and solid sodium borohydride to reduce the aldehyde moiety to give substituted indole-3-carbinol. Substituted DIMs are prepared by condensing the substituted indole-3-carbinol products. This may be achieved, for example, by treatment with a phosphate buffer having a pH of about 5.5. Use of a single indole starting material will lead to symmetrical products, while use of two different indole starting materials will lead to asymmetrical products.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

The term "acyl" includes compounds and moieties that contain the acetyl radical ($CH_3CO$—) or a carbonyl group to which a straight or branched chain lower alkyl residue is attached.

The term "alkyl" as used herein refers to a straight or branched chain, saturated hydrocarbon having the indicated number of carbon atoms. For example, ($C_1$-$C_6$) alkyl is meant to include, but is not limited to methyl, ethyl, propyl, isopropyl, butyl, sec-butyl, tert-butyl, pentyl, isopentyl, neopentyl, hexyl, isohexyl, and neohexyl. An alkyl group can be unsubstituted or optionally substituted with one or more substituents as described herein.

The term "alkenyl" as used herein refers to a straight or branched chain unsaturated hydrocarbon having the indicated number of carbon atoms and at least one double bond. Examples of a ($C_2$-$C_8$) alkenyl group include, but are not limited to, ethylene, propylene, 1-butylene, 2-butylene, isobutylene, sec-butylene, 1-pentene, 2-pentene, isopentene, 1-hexene, 2-hexene, 3-hexene, isohexene, 1-heptene, 2-heptene, 3-heptene, isoheptene, 1-octene, 2-octene, 3-octene, 4-octene, and isooctene. An alkenyl group can be unsubstituted or optionally substituted with one or more substituents as described herein.

The term "alkynyl" as used herein refers to a straight or branched chain unsaturated hydrocarbon having the indicated number of carbon atoms and at least one triple bond. Examples of a ($C_2$-$C_8$) alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein.

The term "alkoxy" as used herein refers to an —O-alkyl group having the indicated number of carbon atoms. For example, a ($C_1$-$C_6$) alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "aminoalkyl" as used herein, refers to an alkyl group (typically one to six carbon atoms) wherein one or more of the $C_1$-$C_6$ alkyl group's hydrogen atoms is replaced with an amine of formula —N($R^c$)$_2$, wherein each occurrence of $R^c$ is independently —H or ($C_1$-$C_6$) alkyl. Examples of aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, —$CH_2CH_2CH_2CH_2CH_2NH_2$, —$CH_2CH_2CH_2CH_2CH_2CH_2NH_2$, —$CH_2CH_2CH_2N$($CH_3$)$_2$, t-butylaminomethyl, isopropylaminomethyl and the like.

The term "aryl" as used herein refers to a 5- to 14-membered monocyclic, bicyclic or tricyclic aromatic ring system. Examples of an aryl group include phenyl and naphthyl. An aryl group can be unsubstituted or optionally substituted with one or more substituents as described herein below. Examples of aryl groups include phenyl or aryl heterocycles such as, dihydropyrimidinone, furan, thiophene, thiazole, isothiazole, imidazole, triazole, tetrazole, pyrazole, oxazole, isoxazole, pyridine, pyrazine, pyridazine, and pyrimidine, and the like.

As used herein, the term "bioactivity" indicates an effect on one or more cellular or extracellular process (e.g., via binding, signaling, etc.) which can impact physiological or pathophysiological processes.

The term "carbonyl" or "carboxy" or "carboxyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "$C_m$-$C_n$" means "m" number of carbon atoms to "n" number of carbon atoms. For example, the term "$C_1$-$C_6$" means one to six carbon atoms ($C_1$, $C_2$, $C_3$, $C_4$, $C_5$ or $C_6$). The term "$C_2$-$C_6$" includes two to six carbon atoms ($C_2$, $C_3$, $C_4$, $C_5$ or $C_6$). The term "$C_3$-$C_6$" includes three to six carbon atoms ($C_3$, $C_4$, $C_5$ or $C_6$).

The term "cycloalkyl" as used herein refers to a 3- to 14-membered saturated or unsaturated non-aromatic monocyclic, bicyclic or tricyclic hydrocarbon ring system. Included in this class are cycloalkyl groups which are fused to a benzene ring. Representative cycloalkyl groups include, but are not limited to, cyclopropyl, cyclobutyl, cyclobutenyl, cyclopentyl, cyclopentenyl, cyclopentadienyl, cyclohexyl, cyclohexenyl, 1,3-cyclohexadienyl, cycloheptyl, cycloheptenyl, 1,3-cycloheptadienyl, 1,4-cycloheptadienyl, -1,3,5-cycloheptatrienyl, cyclooctyl, cyclooctenyl, 1,3-cyclooctadienyl, 1,4-cyclooctadienyl, -1,3,5-cyclooctatrienyl, decahydronaphthalene, octahydronaphthalene, hexahydronaphthalene, octahydroindene, hexahydroindene, tetrahydroinden, decahydrobenzocycloheptene, octahydrobenzocycloheptene, hexahydrobenzocycloheptene, tetrahydrobenzocycloheptene, dodecahydroheptalene, decahydroheptalene, octahydroheptalene, hexahydroheptalene, and tetrahydroheptalene, (1s,3s)-bicyclo [1.1.0]butane, bicyclo[1.1.1]pentane, bicyclo[2.1.1]hexane, Bicyclo[2.2.1]heptane, bicyclo[2.2.2]octane, bicyclo[3.1.1]heptane, bicyclo[3.2.1]octane, bicyclo[3.3.1]nonane, bicyclo[3.3.2]decane, bicyclo [3.3.]undecane, bicyclo[4.2.2]decane, bicyclo [4.3.1]decane. A cycloalkyl group can be unsubstituted or optionally substituted with one or more substituents as described herein below.

The term "halogen" includes fluorine, bromine, chlorine, iodine, etc.

The term "haloalkyl," as used herein, refers to a $C_1$-$C_6$ alkyl group wherein from one or more of the $C_1$-$C_6$ alkyl group's hydrogen atom is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroalkyl," by itself or in combination with another term, means, unless otherwise stated, a stable straight or branched chain alkyl, or combinations thereof, consisting of carbon atoms and from one to three heteroatoms selected from the group consisting of O, N and S, and wherein the nitrogen and sulfur atoms may optionally be oxidized and the nitrogen heteroatom may optionally be quaternized. The heteroatom(s) O, N and S can be placed at any position of the heteroalkyl group. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—$S(O)_2$—$CH_3$, and —$CH_2$—CH=N—$OCH_3$. Up to two heteroatoms can be consecutive, such as, for example, —$CH_2$—NH—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group can be an oxyalkyl group. For instance, ($C_2$-$C_5$) oxyalkyl is meant to include, for example —$CH_2$—O—$CH_3$ (a $C_3$-oxyalkyl group with two carbon atoms and one oxygen replacing a carbon atom), —$CH_2CH_2CH_2CH_2OH$, —$OCH_2CH_2OCH_2CH_2OH$, —$OCH_2CH(OH)CH_2OH$, and the like.

The term "heteroaryl" as used herein refers to an aromatic heterocycle ring of 5 to 14 members and having at least one heteroatom selected from nitrogen, oxygen and sulfur, and containing at least 1 carbon atom, including monocyclic, bicyclic, and tricyclic ring systems. Representative heteroaryls are triazolyl, tetrazolyl, oxadiazolyl, pyridyl, furyl, benzofuranyl, thienyl, benzothienyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, quinoxalinyl and oxazolyl. A heteroaryl group can be unsubstituted or optionally substituted with one or more substituents as described herein below.

As used herein, the term "heteroatom" is meant to include oxygen (O), nitrogen (N), and sulfur (S).

As used herein, the term "heterocycle" refers to 3- to 14-membered ring systems which are either saturated, unsaturated, or aromatic, and which contains from 1 to 4 heteroatoms independently selected from nitrogen, oxygen and sulfur, and wherein the nitrogen and sulfur heteroatoms can be optionally oxidized, and the nitrogen heteroatom can be optionally quaternized, including, including monocyclic, bicyclic, and tricyclic ring systems. The bicyclic and tricyclic ring systems may encompass a heterocycle or heteroaryl fused to a benzene ring. The heterocycle can be attached via any heteroatom or carbon atom, where chemically acceptable. Heterocycles include heteroaryls as defined above. Representative examples of heterocycles include, but are not limited to, aziridinyl, oxiranyl, thiiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thienyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents as described herein below.

The term "heterocycloalkyl," by itself or in combination with other terms, represents, unless otherwise stated, cyclic versions of "heteroalkyl." Additionally, a heteroatom can occupy the position at which the heterocycle is attached to the remainder of the molecule. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "hydroxyalkyl," as used herein, refers to an alkyl group having the indicated number of carbon atoms wherein one or more of the hydrogen atoms in the alkyl group is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "hydroxy" or "hydroxyl" includes groups with an —OH or —$O^-$.

As used herein and unless otherwise indicated, the term "stereoisomer" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. In some embodiments, a stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

As used herein, "protein" is used synonymously with "peptide," "polypeptide," or "peptide fragment". A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, to modulate activity is meant to refer to an increase or decrease in the levels of a peptide or a polypeptide, or to increase or decrease the stability or activity of a peptide or a polypeptide. The term inhibit is meant to refer to a decrease in the levels of a peptide or a polypeptide or to decrease in the stability or activity of a peptide or a polypeptide. The term reduce expression is meant to refer to.

As utilized herein, the term "pharmaceutically acceptable" means approved by a regulatory agency of a federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

A "pharmaceutically acceptable salt" or "salt" of a compound of Formula (I) is a product of the disclosed compound that contains an ionic bond, and is typically produced by reacting the disclosed compound with either an acid or a base, suitable for administering to a subject. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

A "pharmaceutical composition" is a formulation comprising the disclosed compounds in a form suitable for administration to a subject. A pharmaceutical composition of the invention is preferably formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

Substituents for the groups referred to as alkyl, heteroalkyl, alkylene, alkenyl, alkynyl, cycloalkyl, heterocycloalkyl, cycloalkenyl and heterocycloalkenyl can be selected from a variety of groups including —$OR^{d'}$, =O, =$NR^{d'}$, =N—$OR^{d'}$, —$NR^{d'}R^{d''}$, —$SR^{d'}$, -halo, —$SiR^{d'}R^{d''}R^{d'''}$, —OC(O)$R^{d'}$, —C(O)$R^{d'}$, —$CO_2R^{d'}$, —CONR$^{d'}R^{d''}$, —OC(O)NR$^{d'}R^{d''}$, —$NR^{d''}$C(O)$R^{d'}$, —$NR^{d'''}$C(O)NR$^{d'}R^{d''}$, —$NR^{d''''}SO_2NR^{d'}R^{d''}$, —$NR^{d''}CO_2R^{d'}$, —NHC(NH$_2$)=NH, —$NR^{a'}$C(NH$_2$)=NH, —NHC(NH$_2$)=$NR^{d'}$, —S(O)$R^{d'}$, —$SO_2R^{d'}$, —$SO_2NR^{d'}R^{d''}$, —$NR^{d''}SO_2R^{d'}$, —CN and —$NO_2$, in a number ranging from zero to three, with those groups having zero, one or two substituents being exemplary. $R^{d'}$, $R^{d''}$ and $R^{d'''}$ each each independently refer to hydrogen, unsubstituted (C$_1$-C$_8$)alkyl, unsubstituted hetero(C$_1$-C$_8$) alkyl, unsubstituted aryl and aryl substituted with one to three substituents selected from -halo, unsubstituted alkyl, unsubstituted alkoxy, unsubstituted thioalkoxy and unsubstituted aryl (C$_1$-C$_4$)alkyl. When $R^{d'}$ and $R^{d''}$ are attached to the same nitrogen atom, they can be combined with the nitrogen atom to form a 5-, 6- or 7-membered ring. For example, —$NR^{d'}R^{d''}$ can represent 1-pyrrolidinyl or 4-morpholinyl.

Typically, an alkyl or heteroalkyl group will have from zero to three substituents, with those groups having two or fewer substituents being exemplary of the present invention. An alkyl or heteroalkyl radical can be unsubstituted or monosubstituted. In some embodiments, an alkyl or heteroalkyl radical will be unsubstituted.

Exemplary substituents for the alkyl and heteroalkyl radicals include but are not limited to —$OR^{d'}$, =O, =$NR^{d'}$, =N—$OR^{d'}$, —$NR^{d'}R^{d''}$, —$SR^{d'}$, -halo, —$SiR^{d'}R^{d''}R^{d'''}$, —OC(O)$R^{d'}$, —C(O)$R^{d'}$, —$CO_2R^{d'}$, —CONR$^{d'}R^{d''}$, —OC(O)NR$^{d'}R^{d''}$, —$NR^{d''}$C(O)$R^{d'}$, —$NR^{d'''}$C(O)NR$^{d'}R^{d''}$, —$NR^{d''''}SO_2NR^{d'}R^{d''}$, —$NR^{d''}CO_2R^{d'}$, —NHC(NH$_2$)=NH, —$NR^{a'}$C(NH$_2$)=NH, —NHC(NH$_2$)=$NR^{d'}$, —S(O)$R^{d'}$, —$SO_2R^{d'}$, —$SO_2NR^{d'}R^{d''}$, —$NR^{d''}SO_2R^{d'}$, —CN and —$NO_2$, where $R^{d'}$, $R^{d''}$ and $R^{d'''}$ are as defined above. Typical substituents can be selected from: —$OR^{d'}$, =O, —$NR^{d'}R^{d''}$, -halo, —OC(O)$R^{d'}$, —$CO_2R^{d'}$, —C(O)NR$^{d'}R^{d''}$, —OC(O)NR$^{d'}R^{d''}$, —$NR^{d''}$C(O)$R^{d'}$, —$NR^{d''}CO_2R^{d'}$, —$NR^{d'''}SO_2NR^{d'}R^{d''}$, —$SO_2R^{d'}$, —$SO_2NR^{d'}R^{d''}$, —$NR^{d''}SO_2R^{d'}$ —CN and —$NO_2$.

Similarly, substituents for the aryl and heteroaryl groups are varied and selected from: -halo, —$OR^{e'}$, —OC(O)$R^{e'}$, —$NR^{e'}R^{e''}$, —$SR^{e'}$, —$R^{e'}$, —CN, —$NO_2$, —$CO_2R^{e'}$, —C(O)NR$^{e'}R^{e''}$, —C(O)$R^{e'}$, —OC(O)NR$^{e'}R^{e''}$, —$NR^{e''}$C(O)$R^{e'}$, —$NR^{e''}CO_2R^{e'}$, —$NR^{e'''}$C(O)NR$^{e'}R^{e''}$, —$NR^{e'''}SO_2NR^{e'}R^{e''}$, —NHC(NH$_2$)=NH, —$NR^{e'}$C(NH$_2$)=NH, —NH—C(NH$_2$)=$NR^{e'}$, —S(O)$R^{e'}$, —$SO_2R^{e'}$, —$SO_2NR^{e'}R^{e''}$, —$NR^{e''}SO_2R^{e'}$, —$N_3$, —CH(Ph)$_2$, perfluoroalkoxy and perfluoro(C$_1$-C$_4$)alkyl, in a number ranging from zero to the total number of open valences on the aromatic ring system.

$R^{e'}$, $R^{e''}$ and $R^{e'''}$ are independently selected from hydrogen, unsubstituted (C$_1$-C$_8$) alkyl, unsubstituted hetero(C$_1$-C$_8$) alkyl, unsubstituted aryl, unsubstituted heteroaryl, unsubstituted aryl(C$_1$-C$_4$) alkyl and unsubstituted aryloxy (C$_1$-C$_4$) alkyl. Typically, an aryl or heteroaryl group will have from zero to three substituents, with those groups having two or fewer substituents being exemplary in the present invention. In one embodiment of the invention, an aryl or heteroaryl group will be unsubstituted or monosubstituted. In another embodiment, an aryl or heteroaryl group will be unsubstituted.

Two of the substituents on adjacent atoms of an aryl or heteroaryl ring in an aryl or heteroaryl group as described herein may optionally be replaced with a substituent of the formula —T—C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula —J—(CH$_2$)$_r$—K—, wherein J and K are independently —CH$_2$—, —O—, —NH—, —S—, —S(O)—, —S(O)$_2$—, —S(O)$_2$NR$^{f'}$— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR$^{f'}$—, —S—, —S(O)—, —S(O)$_2$—, or —S(O)$_2$NR$^{a'}$—. The substituent R$^{f'}$ in —NR$^{f'}$— and —S(O)$_2$NR$^{f'}$— is selected from hydrogen or unsubstituted (C$_1$-C$_6$) alkyl.

"Stable compound" and "stable structure" are meant to indicate a compound that is sufficiently robust to survive isolation to a useful degree of purity from a reaction mixture, and formulation into an efficacious therapeutic agent.

As used herein the term "therapeutically effective amount" generally means the amount necessary to ameliorate at least one symptom of a disorder to be prevented, reduced, or treated as described herein. The phrase "therapeutically effective amount" as it relates to the compound of Formula (I) of the present invention shall mean the compound of Formula (I) is a dosage that provides the specific pharmacological response for which the compound of Formula (I) is administered in a significant number of subjects in need of such treatment. It is emphasized that a therapeutically effective amount of a compound of Formula (I) that is administered to a particular subject in a particular instance will not always be effective in treating the conditions/diseases described herein, even though such dosage is deemed to be a therapeutically effective amount by those of skill in the art.

The invention encompasses pharmaceutical compositions comprising at least one compound of Formula (I) described herein and at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-compound of Formula (I) active agents.

The pharmaceutical compositions of the invention can comprise compounds of Formula (I) described herein. The compound of Formula (I) can be utilized in any pharmaceutically acceptable dosage form, including but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the compound of Formula (I) described herein can be formulated: (a) for administration selected from the group consisting of oral, pulmonary, intravenous, intra-arterial, intrathecal, intraventricular, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, tinctures, sachets and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) hydroxyl-B-cyclodextrin, or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent (e.g., compound of Formula (I)) in the required amount in an appropriate solvent with one or a combination of ingredients enumerated above, as required, followed by filtered sterilization. Generally, dispersions are prepared by incorporating at least one compound of Formula (I) into a sterile vehicle that contains a basic dispersion medium and any other required ingredients. In the case of sterile powders for the preparation of sterile injectable solutions, exemplary methods of preparation include vacuum drying and freeze-drying, both of which yield a powder of the compound of Formula (I) plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of Formula (I) can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the compound of Formula (I) are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) can also be used as pharmaceutically acceptable carriers.

These can be prepared according to methods known to those skilled in the art, for example, as described in U.S. Pat. No. 4,522,811.

Additionally, suspensions of the compound of Formula (I) may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of compound of Formula (I) calculated to produce the desired therapeutic effect in association with the required pharmaceutical carrier. The specification for the dosage unit forms of the invention are dictated by and directly dependent on the unique characteristics of the compound of Formula (I) and the particular therapeutic effect to be achieved, and the limitations inherent in the art of compounding such an active agent for the treatment of individuals.

Pharmaceutical compositions according to the invention comprising at least one compound of Formula (I) can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, such as Avicel® PH101 and Avicel® PH102, silicified microcrystalline cellulose (ProSolv SMCC™), gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, such as Aerosil® 200, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, Magnasweet® (trademark of MAFCO), bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

Kits Comprising the Compositions of the Invention

The present invention also encompasses kits comprising the compositions of the invention. Such kits can comprise, for example, (1) at least one compound of Formula (I); and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus, such as an inhaler, nebulizer, syringe, etc.

Methods of Treatment

In one embodiment of the invention, a therapeutically effective amount of a compound of formula (I) or a pharmaceutically acceptable salt, stereoisomer, or prodrug thereof, or a pharmaceutical composition comprising a compound of formula (I) or a pharmaceutically acceptable or a pharmaceutically acceptable salt, stereoisomer, or prodrug thereof, is administered to a patient for the prevention and/or treatment of a neurological condition, including a neurological disease, neurological degeneration, neuroinflammation, and/or neuroinflammatory injury related to a neurodegenerative and neurological disease. Such conditions to treat and/or prevent include neurological conditions related to inflammation of glial cells, including inflammatory activation of astrocytes and microglial cells. Neurodegenerative and neurological diseases to prevent and/or treat include Parkinson's disease, Dementia with Lewy Bodies (Lewy Body disease), Multiple System Atrophy, Alzheimer's disease, Vascular Dementia, Huntington's disease, Amyotrophic Lateral Sclerosis (ALS, Lou Gehrig's Disease, Maladie de Charcot), Multiple Sclerosis, neurodegeneration related to stroke, neurodegeneration related to HIV-1 infection, neurodegeneration related to Spinocerebellar Ataxia and Friedrich's Ataxia, neurodegeneration related to Hemiballism (Hemiballismus). In one embodiment, Parkinson's disease can include Parkinsonism, Secondary Parkinsonism, a familial neurodegenerative disease and a 'parkinsonism plus syndrome'.

The compositions of the invention can also be used for prophylactic therapy. Other conditions, diseases and disorders that would benefit from such uses are known to those of skill in the art.

Without being bound by theory, compounds of Formula (I) appear to inhibit NOS2 expression in astrocytes by a mechanism involving interdiction of NF-κB signaling at the level of p65 binding, and through involvement of other transcriptional co-repressors. The present invention shows that that modulation of astrocyte inflammatory phenotype through compound of Formula (I) described herein are effective for suppressing the deleterious effects of activated glia in neurological disease, neurological degeneration, neuroinflammation, and/or neuroinflammatory injury related to neurodegenerative and neurological diseases. One such disease is PD.

Responsiveness of the disease to compound of Formula (I) and compositions comprising compound of Formula (I) can be measured directly by comparison against conventional drugs (for example, for neurological disease, neurological degeneration, neuroinflammation, and/or neuroinflammatory injury), or can be inferred based on an understanding of disease etiology and progression. For example, there are a number of in vitro and in vivo enzyme assays, cell based systems, and animal based systems that are widely accepted in the art as predictive of in vivo effects in humans for the neurological conditions described herein. Thus, the showing that a compound of Formula (I) shows activity in one or more such assays and/or systems is evidence of the clinical utility of these for treating neurological disease, neurological degeneration, neuroinflammation, and/or neuroinflammatory injury.

In one embodiment of the invention, "treatment" or "treating" refers to an amelioration of neurological disease, neurological degeneration, neuroinflammation, and/or neuroinflammatory injury or at least one discernible symptom thereof. In another embodiment, "treatment" or "treating" refers to an amelioration of at least one measurable physical parameter, not necessarily discernible by the patient. In yet another embodiment, "treatment" or "treating" refers to inhibiting the progression of neurological disease, neurological degeneration, neuroinflammation, and/or neuroinflammatory injury, either physically, e.g., stabilization of a discernible symptom, physiologically, e.g., stabilization of a physical parameter, or both. In yet another embodiment, "treatment" or "treating" refers to delaying the onset of cancer or symptoms thereof.

In another embodiment of the invention, "treatment" or "treating" refers to an amelioration of a neurological disease, neurological degeneration, neuroinflammation, and/or neuroinflammatory injury, or at least one discernible symptom thereof. In another embodiment, "treatment" or "treating" refers to an amelioration of at least one measurable physical parameter, not necessarily discernible by the patient.

The compounds of formula (I) or pharmaceutically acceptable salts, solvates, clathrates, and prodrugs thereof can be assayed in vitro or in vivo, for the desired therapeutic or prophylactic activity, prior to use in humans. For example, animal model systems can be used to demonstrate the safety and efficacy of compounds of this invention.

Without wishing to be bound by theory, it is believed that the compounds and compositions of this invention reduce NOS2 gene expression, which has received considerable attention as a potential etiological factor in PD due to its association with nigral degeneration in humans (Knott et al., 2000), as well as the induction of this enzyme in chemical (e.g. MPTP) models of the disease (Liberatore et al., 1999). Without being bound by theory, NO is an important neurotoxic mediator produced by activated astrocytes following challenge with MPTP because inhibiting NOS2 activity or decreasing its expression preserved neuronal viability and prevented the activation of apoptotic signaling pathways.

Accordingly, a number of in vitro and in vitro assays according to the above etiology can be used to test efficacy of compounds of Formula (I). For example, pathology from excess NO is postulated to occur through multiple mechanisms, including reaction with superoxide to form the peroxynitrite anion which can modify tyrosine residues through the formation of covalent 3-nitrotyrosine adducts. Excessive production of NO and subsequent formation of peroxynitrite could therefore interfere with critical homeostatic intracellular processes in astrocytes, as well as damage adjacent neurons. Furthermore, in addition to elevating nitrosative stress in neighboring neurons, astrocyte-derived NO has also been hypothesized to exacerbate neuronal excitotoxicity through potentiation of glutamate release (Duncan and Heales, 2005) and directly inhibits mitochondrial respiration in neurons (Bolanos et al., 1995). Accordingly, the above mentioned biological effects can be used to create, adapt or optimize in vivo and/or in vitro assays to determine the biological activity of diindolylmethane compounds of Formula I, as discussed more fully below.

For example, an assay suitable for determining potential efficacy of a compound of Formula (I) for a neurological disease, neurological degeneration, neuroinflammation, and/or neuroinflammatory injury includes assays using NOS2 as a marker for astrocyte activation. In an example of use of the above assay, DIM-C-pPhtBu was compared to that of an existing thiazoladinedione-class compound, rosiglitazone, which has been previously shown to suppress induction of Nos2. The assay involves use of primary cultured astrocytes and activation by an MPTP (10 µM), TNF-α (10 pg/ml) and IFN-γ (1 ng/ml) combination to determine a dose-responsive suppression of Nos2 to determine the activity of putative efficacious diindolylmethane-class compounds of the present invention. Another assay includes measurement of suppression of NOS2 protein levels in primary astrocytes activated with MPTP and inflammatory cytokines.

For example, an assay suitable for determining potential efficacy of diindolylmethane compounds of Formula (I) for neurological disease, neurological degeneration, neuroinflammation, and/or neuroinflammatory injury include assays for intracellular nitration. NOS2 expression plays a role in protein dysregulation; because astrocytes perform tasks vital to the survival and function of neurons, increased protein nitration within this cell can, without being bound by theory, negatively impact neuronal survival. One example of an intracellular nitration assay includes testing for nitration in primary cultured astrocytes by immunofluorescence using antibodies against 3-nitrotyrosine, to reveal an increase in global protein nitration following treatment of the cells with the MPTP and TNF-α/IFN-γ, and potential suppression of this effect by diindolylmethane compounds of Formula (I.) One such way to quantify the effect is by immunoblotting.

For example, an assay suitable for determining potential efficacy of diindolylmethane compounds of Formula (I) for neurological disease, neurological degeneration, neuroinflammation, and/or neuroinflammatory injury include assays for activation of the NF-κB signaling cascade. The NF-κB signaling cascade is linked to the induction of wide array of stress-response genes and is recognized to be a key event in the expression of Nos2. Activation of NF-κB in astrocytes treated with MPTP and inflammatory cytokines can be measured in astrocytes isolated from a transgenic mouse which expresses EGFP in response to multiple cis-acting NF-κB domains. Live-cell fluorescence imaging can be used to detect increased NF-κB-dependent GFP expression in astrocytes challenged with MPTP and TNF-α/IFN-γ cytokines Compounds of the present invention can be used to detect suppression of NF-κB-dependent GFP expression in astrocytes challenged with MPTP and TNF-α/IFN-γ cytokines and compared to rosiglitazone.

For example, an assay suitable for determining potential efficacy of diindolylmethane compounds of Formula (I) for neurological disease, neurological degeneration, neuroinflammation, and/or neuroinflammatory injury includes an assay for model of astrocyte-mediated neurodegeneration, where astrocytes activated by exposure to MPTP and inflammatory cytokines are co-incubated with GADD65/67-positive primary striatal neurons. Astrocytes stimulated in this manner cause increases in caspase activity and Annexin V reactivity in co-cultured neurons, along with a consistently observed general decrease in the number of live neurons. Co-treatment with, for example, DIM-C-pPhOCH3 or DIM- C-pPhtBu can be carried out to detect decreased neuronal caspase activity compared to rosiglitazone or the NOS2 inhibitor, AMT, which can be confirmed by Annexin V staining This assay demonstrates that compounds of Formula (I) effectively counter the neuro-inflammatory effects of MPTP and TNF-α/IFN-γ in astrocytes and thereby prevents the degeneration of co-cultured striatal neurons.

For example, an assay suitable for determining efficacy of diindolylmethane compounds of Formula (I) includes the transgenic NF-κB/GFP reporter mouse model (C57B1/6 background). After treatment with a compound of Formula (I), mice can be assessed, for example, for activation of astrocytes, expression of NOS2, and expression of GFP. Also, C57B1/6 mice may be assessed for reduction of 3-nitrotyrosine protein adducts after treatment with a compound of Formula (I).

The inventor observed that for compounds of Formula (I), suppression of NF-κB activation occurred in astrocytes challenged with MPTP and TNF-α/IFN-γ, when co-treated with rosiglitazone. Rosiglitazone acts to prevent the induction of macrophage Nos2 through recruitment of PPAR-γ to the promoter region that subsequently stabilized NCoR2. In contrast, the compounds of Formula (I) tested failed to recruit PPAR-γ or stabilize NCoR2, and prevented the binding of p65 to the Nos2 promoter. Without being bound by theory, this finding shows a mechanism of transrepression of NF-κB distinct for compounds of Formula (I) from that reported for rosiglitazone compounds such that interdiction of NF-κB signaling may occur either upstream of transcriptional repressor stabilization or may involve nuclear factors distinct from those currently identified as targets of PPAR-γ.

These results are consistent with the ongoing studies with PPAR-γ-active C-DIMs in which many of their activities are PPAR-γ-independent and involve activation of kinases, decreased mitochondrial membrane potential, and induction of endoplasmic reticulum stress. By blocking binding of p65, without being bound by theory, DIM-C-pPhtBu may thereby suppress a larger array of NF-κB-responsive genes than rosiglitazone compounds.

The patient can be any animal, domestic, livestock or wild, including, but not limited to cats, dogs, horses, pigs and cattle, and preferably human patients. As used herein, the terms patient and subject may be used interchangeably.

In one embodiment, compounds of Formula (I) may be administered in combination therapy with agents known for the treatment of neurological conditions. For example, one or more compounds of Formula (I) may be administered together with agents known for the treatment of Parkinson's disease, such as, for example, L-DOPA, a decarboxylase inhibitor, bromocriptine, pergolide as a dopamine agonist, and/or anticholinergic agents such as trihexyphenidyl (artane). For example, one or more compounds of Formula (I) may be administered together with agents known for the treatment of Alheimer's disease, such as, for example, tacrine (Cognex), donepezil (Aricept), rivastigmine (Exelon) galantamine (Reminyl/Razadyne), memantine (Namenda/Exiba), neramexane (1,3,3,5,5-pentamethylcyclohexan-1-amine). In one embodiment, compounds of Formula (I) may be administered together with an anti-inflammatory agent, such as, for example, nonsteroidal antiinflammatory drugs (NSAIDs), COX-2 inhibitors, and anti-inflammatory steroidal drugs.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated. All references cited herein are incorporated in their entirety by reference.

EXAMPLES

The following examples are provided for illustrative purposes only and are not intended to limit the scope of the invention.

Example 1

Synthesis of Diindolylmethane

Indole or ring-substituted indoles (e.g., 5-methoxy, 5-chloro, 5-bromo, 5-fluoro, 5-methyl, 5-nitro, N-methyl and 2-methyl) are commercially available and these compounds are used for synthesis of diindolylmethane analogs. Alkyl, substituted alkyl, aromatic, or substituted aromatic aldehydes (0.01 mole) are incubated with indole or a substituted indole (0.02 mole) in water (50 ml) plus glacial acetic acid (0.5 ml). Depending on the structure of the aldehyde or indole, the reaction is continued with stirring for 2 days to 2 weeks. The reaction product is either filtered or isolated by extraction with chloroform and the residue crystallized from benzene/petroleum spirit. The resulting substituted DIM is then used in in vivo or in vitro studies. DIMs tend to be photosensitive and should be stored in dark brown vials.

Example 2

Methods

Materials: Unless otherwise stated, all reagents were purchased from Sigma-Aldrich Chemical Co. (St. Louis, Mo.). DIM-C-pPhtBu was synthesized as previously described (Qin et al., 2004), and rosiglitazone was purchased from Cayman Chemical (Ann Arbor, Mich.). The NOS2 inhibitor 2-amino-5,6-dihydro-6-methyl-4H-1,3-thiazine (AMT) was purchased from Calbiochem (San Diego, Calif.). Cell culture media, antibiotics, and fluorescent antibodies and dyes were purchased from Invitrogen (Carlsbad, Calif.).

Monoclonal antibodies against NOS2 were purchased from BD biosciences (San Jose, Calif.). Horseradish peroxidase conjugated goat anti-mouse secondary antibodies were purchased from Santa Cruz Biotechnology (Santa Cruz, Calif.). For immunofluorescence studies, antibodies against glial fibrillary acidic protein (GFAP), 3-nitrotyrosine, ionized calcium binding adapter molecule 1 (Iba1), and Gad63/67 and p65 were purchased from Sigma Chemical Co. (St. Louis, Mo.), Chemicon (Temecula, Calif.), Wako Pure Chemical Industries, Ltd. (Tokyo, Japan), and Santa Cruz Biotechnology (Santa Cruz, Calif.) respectively. Antibodies used for ChIP analysis of p65, PPAR-γ, and NCoR2 were purchased from Santa Cruz Biotechnology (Santa Cruz, Calif.), Cell Signaling Technology (Danvers, Mass.), and Abcam (Cambridge, Mass.), respectively.

Figure 2:
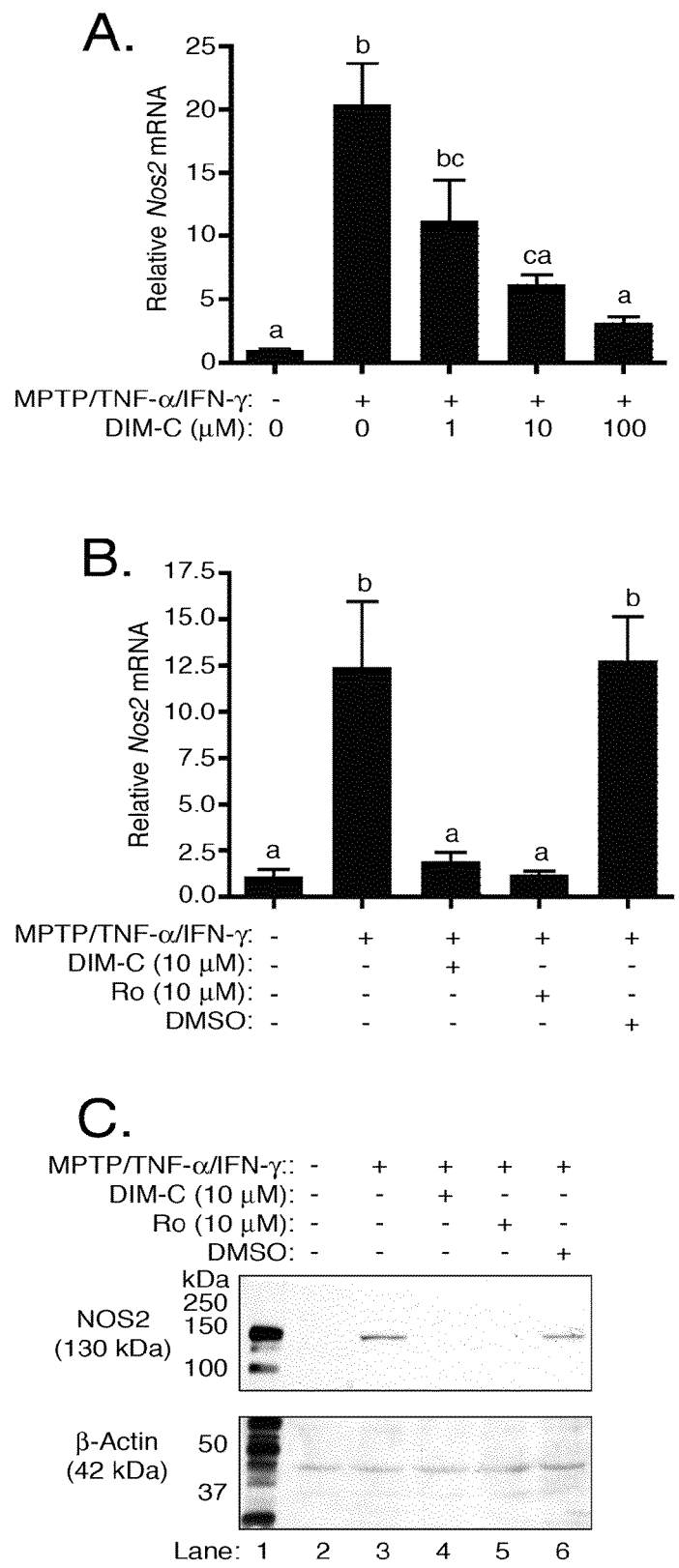
FIG. 2(A) shows a semi-quantitative real-time RT-PCR demonstrating dose-responsive suppression of Nos2 mRNA by concentrations of DIM-C-pPhtBu ranging from 1 to 10 μM in astrocytes challenged with MPTP, TNF-α, and IFN-γ.
FIG. 2(B) shows semi-quantitative real-time PCR demonstrating equivalent suppression of Nos2 mRNA by either DIM-C-pPhtBu or rosiglitazone in astrocytes challenged with MPTP, TNF-α, and IFN-β.
FIG. 2(C) shows that immunoblotting demonstrates suppression of NOS2 protein expression by either DIM-C-pPhtBu or rosiglitazone in astrocytes exposed to MPTP and TNF-α/IFN-γ (Lane 4-5). Activated macrophage lysate was used as a positive control for identification of NOS2 (Lane 1). All quantitative PCR and western blotting experiments were performed three times (n=3).

Primary Cell Isolation. Cortical astrocytes were isolated from day-1 old C57B1/6 or transgenic mouse pups according to procedures described previously (Aschner and Kimelberg, 1991), and purity confirmed through immunofluorescent staining using antibodies against GFAP and Iba1. Briefly, pups were euthanized by decapitation under isofluorane anesthesia and cortices (astrocytes) or striatum (neurons) rapidly dissected out, and meninges removed. Tissue was subject to digestion with Dispase (1.5 U/ml), and selection of astrocytes was performed by complete media change 24 hrs after plating to remove non-astroglial cell types by serum shock. This method routinely results in cultures that are approximately 99% pure astrocytes, with less than 1% contaminating microglial cells (Supplementary FIG. 1). Astrocyte cultures were maintained at 37° C. and 5% CO2 in minimum essential media supplemented with 10% heat-inactivated fetal bovine serum and a penicillin (0.001 mg/ml), streptomycin (0.002 mg/ml), and neomycin (0.001) antibiotic cocktail. Cell media was changed 24 hrs prior to all treatments. Primary neuronal cultures were seeded onto poly-L-lysine-coated 30 mm glass coverslips at 4×105 cells per well, and maintained in neurobasal media supplemented with 2 mM L-glutamine, a B27 supplement, and a penicillin (0.001 mg/ml), streptomycin (0.002 mg/ml), and neomycin (0.001) antibiotic cocktail. Neuronal culture media was changed 24 hours after isolation and every two days afterward, and culture purity confirmed through cell morphology and immunostaining against GAD65/67 (Supplementary FIG. 2). Neurons were used within two weeks of plating. All animal procedures were approved by the Colorado State University Institutional Animal Care and Use Committee, and were conducted in accordance with published NIH guidelines.

RT and Real-Time RT-PCR. Astrocytes were treated with MPTP (10 µM) and the inflammatory cytokines TNF-α (10 pg/ml) and IFN-γ (1 µg/µl), with or without DIM-C-pPhtBu (1, 10, or 100 µM), rosiglitazone (10 µM), or a DMSO vehicle control for three hours prior to RNA isolation. RNA was isolated using the RNEasy Mini kit (Qiagen, Valencia, Calif.), and purity and concentration were determined using a Nanodrop ND 1000 spectrophotometer (NanoDrop Technologies, Wilmington, Del.). Following purification, 1 ug of RNA was used as template for reverse transcriptase (RT) reactions using the iScript RT kit (BioRad, Hercules Calif.). The resulting cDNA was immediately profiled for Nos2 gene expression (forward: 5'-TCACGCTTGGGTCTTGTT-3' (SEQ ID NO:1); reverse: 5'-CAGGTCACTTTGGTAGGATTT -3'3' (SEQ ID NO:2)) using β-Actin as a housekeeping gene (forward: 5'-GCTGTGCTATGTTGCTCTAG-3'3' (SEQ ID NO:3); reverse: 5'-CGCTCGTTGCCAATACTG-3'3' (SEQ ID NO:4)) according to the $2^{-\Delta\Delta CT}$ method (Livak and Schmittgen, 2001).

Western Blotting. Astrocytes were treated with MPTP (10 µM) and the inflammatory cytokines TNF-α (10 pg/ml) and IFN-γ (1 ng/ml), with or without DIM-C-pPhtBu (10 µM), rosiglitazone (10 µM), or a DMSO vehicle control for eight hours prior to protein harvesting. Cells were lysed using a triple detergent lysis buffer (50 mM Tris-HCl, pH 8.1, 150 mM NaCl, 0.1% SDS, 1.0% NP-40, and 0.5% sodium deoxycholate) supplemented with Complete™ protease inhibitor (Roche, Indianapolis Ind.). Protein was quantified using the BCA assay (Pierce, Rockford Ill.), and 20 µg of protein were separated by standard SDS-PAGE using a 6% slab gel (BioRad, Hercules Calif.) followed by semi-dry transfer to polyvinylidene fluoride (PVDF) membrane (Pall Corp., Pensacola, Fla.). All blocking and antibody incubations were performed in 5% non-fat dry milk in tris-buffered saline containing 0.2% Tween-20. A positive control consisting of 0.5 µg activated macrophage lysate (BD Biosciences, San Jose, Calif.) was included to confirm results. Protein was visualized on film using enhanced chemiluminescence (Pierce, Rockford, Ill.).

Immunofluorescence. Primary astrocytes were grown to confluence on 20 mm serum-coated glass coverslips and treated with saline or MPTP (10 µM), TNF-α (10 pg/ml), and IFN-γ (1 ng/ml) with or without DIM-C-pPhtBu (10 µM), rosiglitazone (10 µM), the NOS2 inhibitor AMT (25 nM) or NOS 1 inhibitor 7-NI (10 µM), or a DMSO vehicle control 8 hours prior to analysis. Immunofluorescence to confirm culture purity was conducted on cells grown to confluence on the 20 mm glass coverslips. Blocking and antibody hybridization was conducted in 1% BSA (w/v) in PBS, and all washes were conducted in PBS. Images were acquired using a Zeiss 20× air PlanApochromat objective and 6-8 microscopic fields were examined per treatment group over no less than three independent experiments. Fluorescent secondary antibodies were used to detect GFAP (488 nmcx/519 nmcm) and Iba1 or nitrosylated protein (647 nmcx/668 nmcm), respectively, while mounting medium containing DAPI (360 nmcx/460 nmcm) was used to identify cell nuclei.

NF-κB reporter assays in cis-NF-κB$^{EGFP}$ transgenic astrocytes and expression of mutant IκBα. To measure activation of NF-κB in live cell, astrocytes were isolated from a unique transgenic mouse expressing a reporter construct consisting of three HIV NF-κB consensus elements inserted 5' to a minimal c-fos promoter that drives expression of enhanced green fluorescent protein (EGFP) (Magness et al., 2004) (Provided by Dr. Christian Jobin, University of North Carolina at Chapel Hill). NF-κB activity was determined by live-cell imaging using a Zeiss 20× air PlanApochromat objective using SlideBook v4.2 (Intelligent Imaging Innovations, Inc., Denver, Colo.). Image saturation was prevented by 1) minimizing exposure time, 2) using the digital gain on the CCD to enhance sensitivity, and 3) carefully monitoring the exposure histogram to insure that pixel intensities did not approach saturation. This approach was consistent between all replicates. At least four microscopic fields were examined per treatment group in each of at least three independent experiments, and reported as percent activated cells 8 hours following treatments. A phosphorylation-deficient mutant of IκBα, IκBa-(S32,36A)-HA, was overexpressed in primary astrocytes using an adenoviral vector, delivered for 24 hrs at 2×10$^6$ viral particles per ml of culture medium, with a multiplicity of infection of 1×10$^3$ virions per cell shown previously by us to result in expression of the mutant protein by over 99% of the astrocytes (Barhoumi et al., 2004). Parallel control experiments utilized the same adenoviral construct lacking the insert. Following incubation with the mutant IκBα construct for 24 hrs, astrocytes were washed with PBS to remove viral particles and cultured in fresh medium for 24 hrs prior to use.

Chromatin Immunoprecipitation (ChIP). ChIP procedures were adapted from a previously published report (Weinmann and Farnham, 2002) and optimized for primary astrocytes according to recent studies from our laboratory. Astrocytes were grown to confluence in 10 cm plates (Approx. 8.8×10$^6$ cells) and were treated for 3 hours with MPTP (10 µM), TNF-α (10 pg/ml) and IFN-γ (1 ng/ml) with or without DIM-C-pPhtBu (10 µM), rosiglitazone (10 µM) or a DMSO vehicle control for 3 hours prior to analysis. DNA was sheared into approximate 500 bp fragments by three ten-second pulses using a Tekmar Sonic Disrupter (Tekmar Co., Cincinnati, Ohio) set at 30% output, followed by collection of 10% input controls and addition of 2 µg precipitating antibody. Immune complexes were allowed to form overnight at 4° C. with gentle agitation, followed by the addition of protein-G magnetic beads (Active Motif, Carlsbad, Calif.) for an additional 90 min. Immunopurified DNA was isolated via phenol/chloroform extraction and subject to PCR using primers designed around the proximal murine Nos2 NF-κB binding region (Xie et al., 1992) (forward: 5'-ATG GCC TTG CAT GAG GAT ACA CCA-3' Chromatin Immunoprecipitation (ChIP). ChIP procedures were adapted from a previously published report (Weinmann and Farnham, 2002) and optimized for primary astrocytes according to recent studies from our laboratory. Astrocytes were grown to confluence in 10 cm plates (Approx. $8.8 \times 10^6$ cells) and were treated for 3 hours with MPTP (10 μM), TNF-α (10 pg/ml) and IFN-γ (1 ng/ml) with or without DIM-C-pPhtBu (10 μM), rosiglitazone (10 μM) or a DMSO vehicle control for 3 hours prior to analysis. DNA was sheared into approximate 500 bp fragments by three ten-second pulses using a Tekmar Sonic Disrupter (Tekmar Co., Cincinnati, Ohio) set at 30% output, followed by collection of 10% input controls and addition of 2 μg precipitating antibody. Immune complexes were allowed to form overnight at 4° C. with gentle agitation, followed by the addition of protein-G magnetic beads (Active Motif, Carlsbad, Calif.) for an additional 90 min. Immunopurified DNA was isolated via phenol/chloroform extraction and subject to PCR using primers designed around the proximal murine Nos2 NF-κB binding region (Xie et al., 1992) (forward: 5'-ATG GCC TTG CAT GAG GAT ACA CCA-3'(SEQ ID NO:5); reverse: 5'-GAG TCT CAG TCT TCA ACT CCC TGT-3'(SEQ ID NO:6)). Amplicons were separated by 2% agarose gel electrophoresis and stained with ethidium bromide.

Astrocyte Neuron Co-Culture. Cells were isolated as described above and astrocytes grown to confluence on permeable cell culture inserts (BD Biosciences, San Jose, Calif.) prior to treatment. Astrocytes were then treated with MPTP (10 μM), TNF-α (10 pg/ml) and IFN-γ (1 ng/ml) in the presence or absence of DIM-C-pPhtBu (10 μM), Rosiglitazone (10 μM) AMT (25 nM), or DMSO vehicle control for 8 hours. Media was then removed, and the astrocytes washed three times with sterile PBS to prevent carryover of treatment medium to the neurons, and the inserts were placed directly in each well over cultured neurons. Astrocyte-containing inserts were removed following six hours of co-culture, and neuronal caspase activity and phosphatidylserine translocation were measured by widefield fluorescence microscopy using the general cell permeable fluorescent caspase substrate rhodamine 110, bis-(L-aspartic acid amide) and an Annexin V Alexa Fluor 680 conjugate, respectively. Images were acquired using a Zeiss 20× air PlanApochromat objective and at least 10 microscopic fields were examined per treatment group over three independent experiments.

Statistical Comparisons.

Experiments were performed no less than three times, with replicates consisting of independent cultures using a minimum of four plates or cover slips per replicate study. Comparison of two means was performed by Student's t-test, while comparison of three or more means was performed using one-way ANOVA followed by the Tukey-Kramer multiple comparison post-hoc test using Prism software (v4.0c, Graphpad Software, Inc., San Diego, Calif.). For all experiments, $p<0.05$ was considered significant, although the level of significance was often much greater. Statistically different groups are identified in the figures by the assignment of a unique letter (e.g., a, b, c, d).

Isolation of Primary Astrocytes and Neurons. The purity of primary astrocyte cultures isolated according to the procedures described previously (Aschner and Kimelberg, 1991) were assayed for microglial contamination through dual immunofluorescent staining against GFAP (FITC) or Iba1 (Cy5) (Supplementary FIG. 1A), demonstrating approximately 99% culture purity (Supplementary FIG. 1B), with less than 1% Iba1-positive microglial cells.

Example 3

Modulation of NOS2 Expression by DIM-C-pPhtBu.

Semi-quantitative real-time RT-PCR analysis indicated that exposure of astrocytes to MPTP and TNF-cα/IFN-γ resulted in a large increase in expression of Nos2 mRNA that was dose-dependently suppressed by concentrations of DIM-C-pPhtBu ranging from 1 to 100 μM (FIG. 2A). Because co-treatment with 10 μM DIM-C-pPhtBu represented the lowest dose that suppressed Nos2 induction to levels statistically indistinguishable from saline-treated control astrocytes, this concentration was used to compare efficacy with an equivalent concentration of the traditional thiazoladinedione PPAR-γ agonist, rosiglitazone. Real-time PCR demonstrated equivalent suppression of Nos2 to levels observed in saline-treated control astrocytes by both DIM-C-pPhtBu and rosiglitazone, whereas the DMSO vehicle control had no suppressive effect on induction (FIG. 2B). Immunoblotting demonstrated similar suppression of NOS2 protein by both DIM-C-pPhtBu and rosiglitazone in astrocytes exposed to MPTP and TNF-α/IFN-γ (FIG. 2C).

Example 4

Suppression of NOS2-Mediated Protein Nitration.

Figure 3:
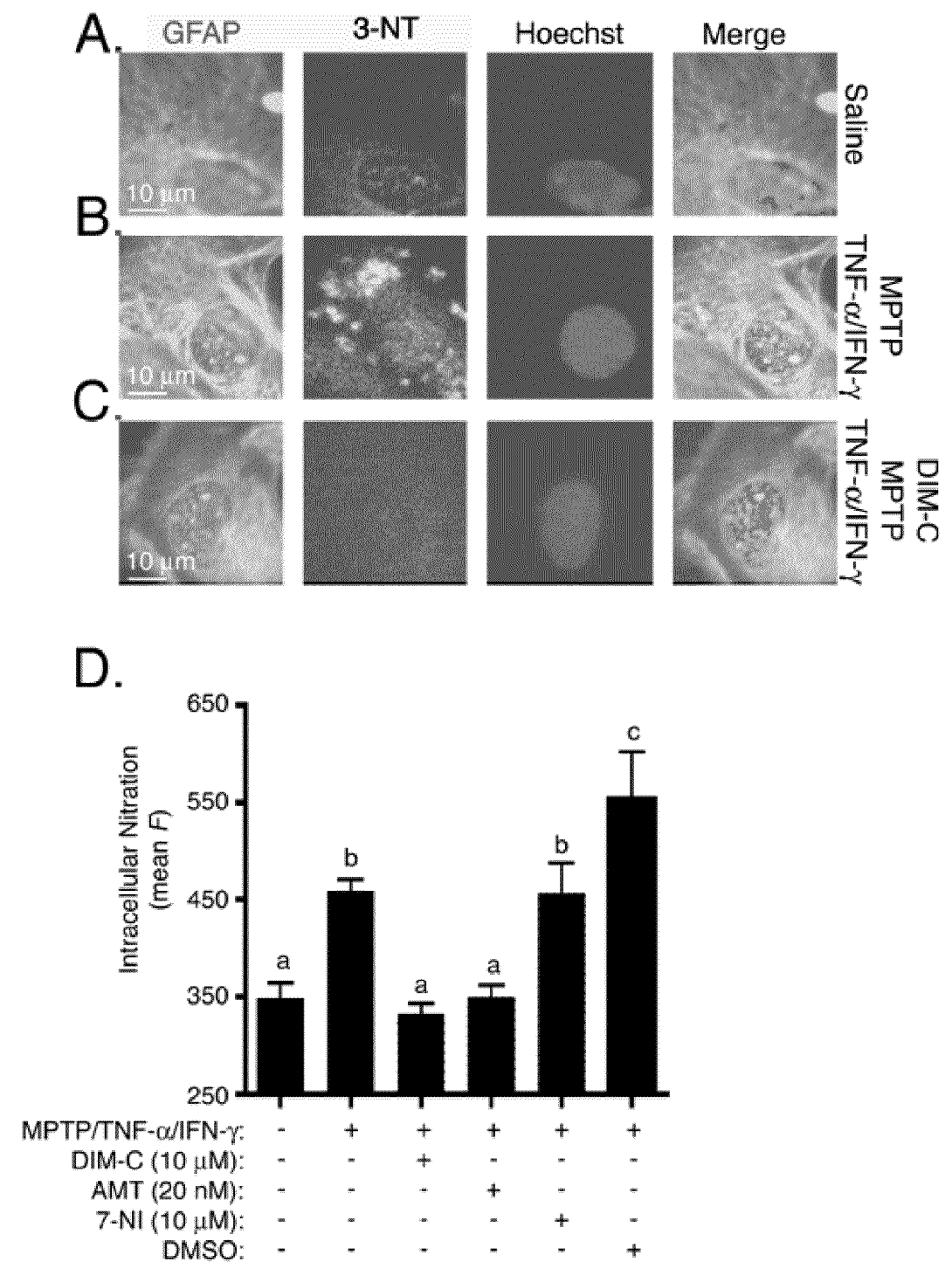
FIG. 3(A) shows immunofluorescence detection of GFAP and 3-Nitrotyrosine (3-NT;) revealing in FIG. 3(B) an increase in nitration in astrocytes treated with MPTP and TNF-α/IFN-γ, and 3(C) suppression of nitration to control levels following co-treatment with DIM-C-pPhtBu.
FIG. 3(D) shows quantitation of 3-NT fluorescence demonstrating a significant elevation in nitration in activated astrocytes and suppression of this effect by DIM-C-pPhtBu or the NOS2 inhibitor AMT, but not the NOS 1 inhibitor 7-NI, implicating NOS2 in the elevated nitration. Imaging studies presented in this figure were performed three times (n=3), and between 4-6 images captured per experiment for internal repetition.

The effect of NOS2 induction by MPTP and inflammatory cytokines on global protein nitration following NO/peroxynitrite (ONOO—) formation in astrocytes was examined by immunofluorescence (FIG. 3). Immunofluorescence using antibodies against GFAP (FITC) and 3-nitrotyrosine adducts (Cy5) was employed to measure the extent of protein nitration within astrocytes treated with MPTP and cytokines, with or without inclusion of DIM-C-pPhtBu (10 μM), rosiglitazone (10 μM), the high-affinity NOS2 inhibitor AMT (25 nM), the NOS1 inhibitor 7-NI (10 μM) or a DMSO vehicle control. Minimal levels of protein nitration were detected in saline-treated control astrocytes (FIG. 3A), whereas astrocytes challenged with MPTP and cytokines demonstrated a significant elevation in internal protein nitration (FIG. 3B). Co-treatment of astroytes with DIM-C-pPhtBu prevented MPTP-induced increases in nitration, resulting in similar levels of 3-nitrotyrosine adducts as saline-treated control cells (FIG. 3C). Mean intracellular fluorescence for 3-nitrotyrosine was quantified and compared between each treatment group (FIG. 3D). The MPTP-induced increase in 3-nitrotyrosine formation was prevented in astrocytes co-treated with either DIM-C-pPhtBu (10 μM) or the NOS2 inhibitor AMT (25 nM), but not the NOS1 inhibitor 7-NI (10 μM), to levels observed in saline-treated astrocytes, demonstrating suppression of internal protein nitration by DIM-C-pPhtBu. The DMSO vehicle control did not suppress MPTP-induced increases in the 3-nitrotyrosine fluorescence signal but rather increased signal somewhat above that induced by treatment with MPTP and TNF-α/IFN-γ alone.

Example 5

Inhibition of the NF-κB Signaling Pathway.

Figure 4A:
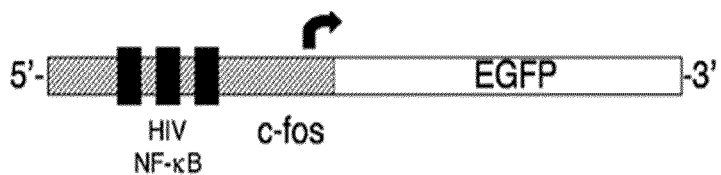
FIG. 4 shows activation of NF-κB in response to the MPTP and cytokine insult measured by live-cell fluorescence imaging using primary astrocytes isolated from transgenic mice which express an EGFP reporter construct driven by multiple cis-acting NF-κB domains (FIG. 4(A)).
FIG. 4(B) shows that NF-κB is activated in astrocytes exposed to MPTP and TNF-α/IFN-γ but co-treatment with either DIM-C-pPhtBu or rosiglitazone suppresses this activation, whereas DMSO vehicle control had no effect.
FIG. 4(C) shows that expression of mutant IκBα (S32/36A; an NF-κB 'super repressor') by adenoviral transfection suppressed induction of Nos2 mRNA but an empty control vector had no suppressive effect.
FIG. 4(D) shows expression of EGFP in transgenic astrocytes exposed to MPTP and inflammatory cytokines in the presence of mutant IκBα or control construct. Imaging studies using transgenic cells were performed three times (n=3), and 4 images per chamber captured for internal replicate.
Figure 4B:
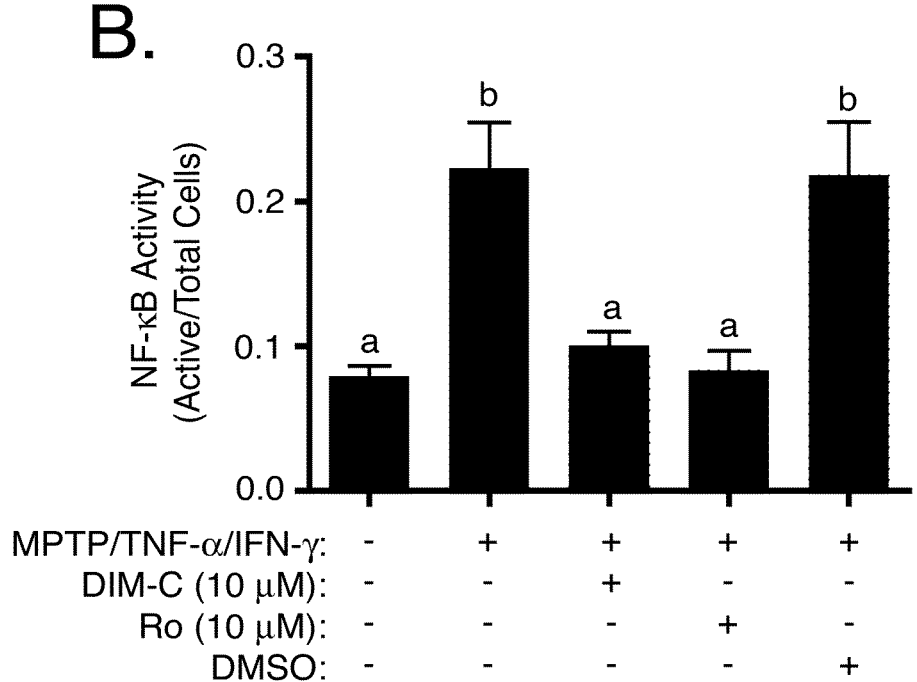
Figure 4C:
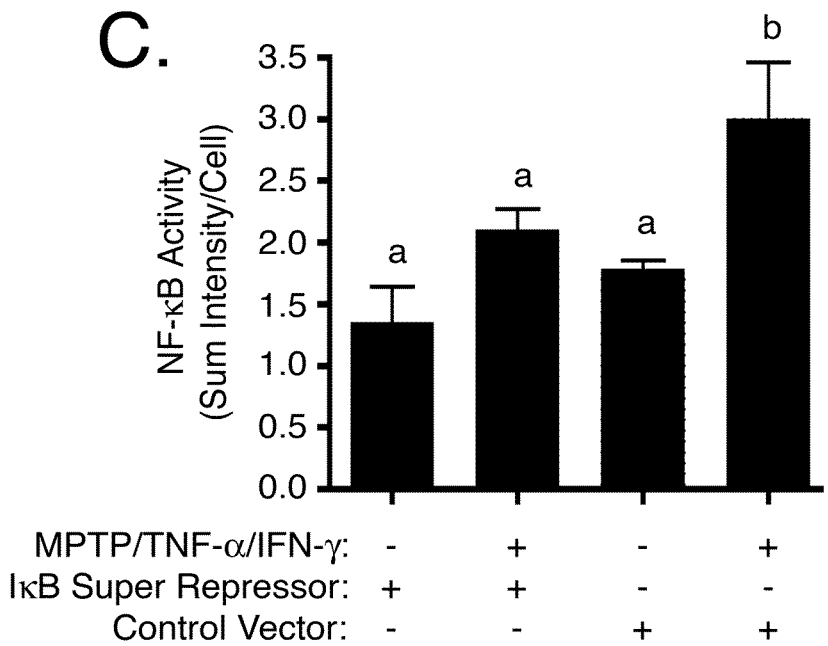
Figure 4D:
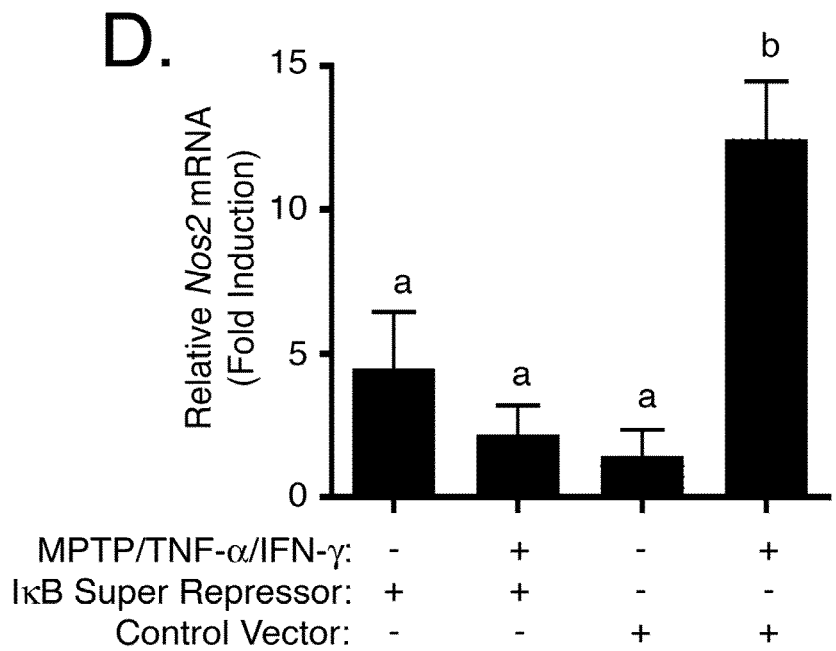

A wide array of inflammatory genes, including Nos2, are driven by the NF-κB signaling cascade. To explore the efficacy of DIM-C-pPhtBu in modulating this pathway, we employed astrocytes isolated from a transgenic mouse that expresses an EGFP construct driven by multiple cis-acting NF-κB domains (FIG. 4A) (Magness et al., 2004). Real-time imaging of GFP fluorescence was performed in control transgenic astrocytes exposed to saline and in cells exposed to MPTP and TNF-α/IFN-γ in combination with DIM-C-pPhtBu (10 µM), rosiglitazone (10 µM), or DMSO. (FIG. 4B). Exposure to MPTP+TNF-α/IFN-γ resulted in an approximate 2.5-fold increase in total cellular GFP fluorescence compared to control cells that was completely suppressed by either DIM-C-pPhtBu or rosiglitazone but not by DMSO. As a control for the specificity of the cis-NF-KB$^{EGFP}$ construct for NF-κB-dependent signaling, transgenic astrocytes were transfected with mutant IκBα (S32/36A) to prevent activation of NF-κB. Cells expressing mutant IκBα failed to respond to MPTP and TNF-α/IFN-γ with an increase in GFP fluorescence, whereas GFP fluorescence increased markedly in transgenic astrocytes transfected with a control adenoviral vector (FIG. 4C). Similarly, challenge with MPTP and cytokines in astrocytes isolated from wild type C57/B16 mice expressing mutant IκBα did not result in an increase in Nos2 mRNA, whereas a similar exposure in astrocytes expressing an empty control vector resulted in a significant increase in Nos2 mRNA (FIG. 4D).

Example 6

Chromatin Immunoprecipitation (ChIP) Analysis of the Nos2 Promoter.

Figure 5:
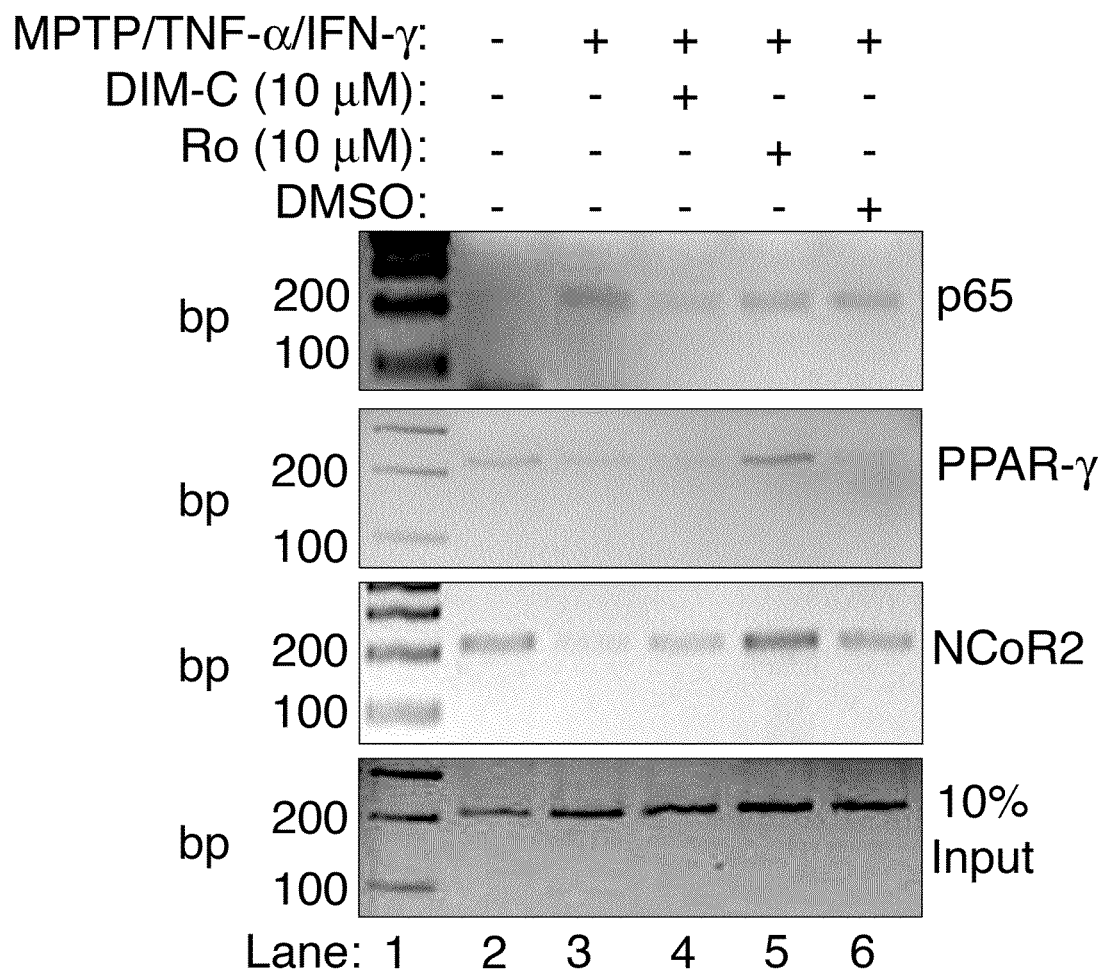
FIG. 5 shows chromatin immunoprecipitation (ChIP) revealing binding of p65 to the proximal NF-κB enhancer element in the Nos2 promoter along with removal of NCoR2 following challenge of astrocytes with MPTP and TNF-α/IFN-γ, (Lane 3). Co-treatment of the astrocytes with DIM-C-pPhtBu resulted in prevention of p65 docking (Lane 4), however, no effect on PPAR-γ recruitment or NCoR2 stabilization was observed. In contrast, co-treatment of astrocytes with rosiglitazone (Lane 5) did not affect p65 docking, however, this treatment did result in recruitment of PPAR-γ and ensuing stabilization of NCoR2. These data demonstrate different mechanisms of Nos2 gene suppression by DIM-C-pPhtBu and rosiglitazone. ChIP experiments were repeated three times (n=3) using individual cultures, and the presented data are representative of the results.

To determine the mechanism by which DIM-C-pPhtBu modulates NF-κB activity, the ChIP assay was used to identify specific DNA-protein interactions at the proximal NF-κB enhancer element (-86 to -76) of the Nos2 promoter. Based upon previous studies demonstrating a requirement for degradation of the nuclear co-repressor 2 protein (NCoR2) at the p65 binding site during NF-κB-dependent transactivation (Pascual et al., 2005), we examined binding of this factor, as well as that of p65 and PPAR-γ, to the proximal NF-κB response element during challenge with MPTP and cytokines in the absence and presence of DIM-C-pPhtBu or Rosaglitazone (FIG. 5). These data demonstrate that treatment with MPTP and cytokines induced binding of p65 to the Nos2 promoter (FIG. 5, Lane 3) that was blocked by co-treatment with DIM-C-pPhtBu (10 µM) but not rosiglitazone (10 µM) (FIG. 5, Lane 4-5). However, DIM-C-pPhtBu did not recruit PPAR-γ to this promoter region, nor did it stabilize NCoR2 (FIG. 5, lane 4, panels 2 and 3). In contrast, rosiglitazone recruited PPAR-γ to the proximal NF-KB response element and prevented degradation of NCoR2 (FIG. 5, panels 2 and 3, lane 5). These data demonstrate a mechanism of inflammatory suppression by DIM-C-pPhtBu distinct from that of rosiglitazone.

Example 7

Astrocyte and Neuron Co-Culture.

Figure 6:
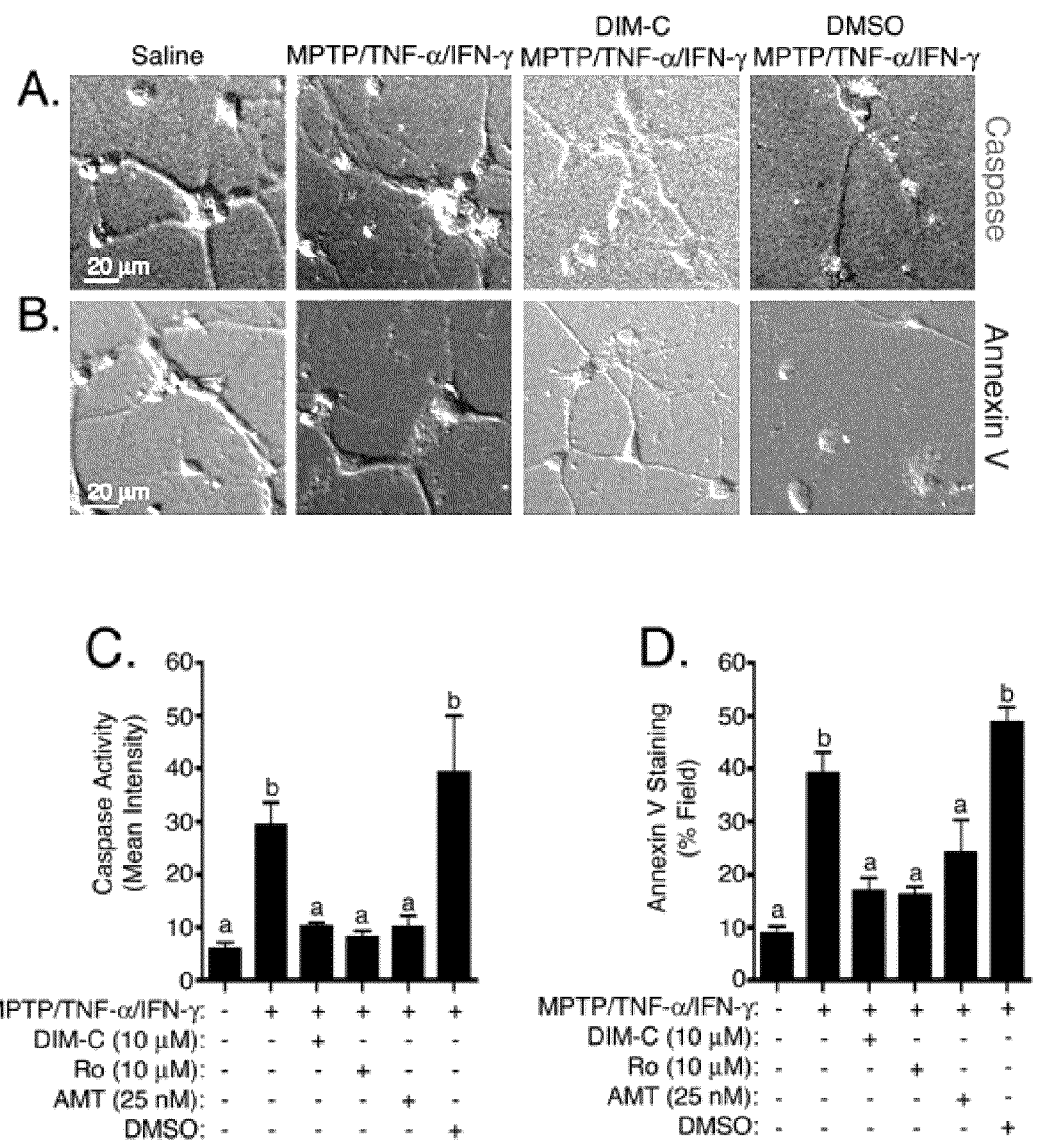
FIG. 6 shows caspase activity (FIG. 6(A)) and annexin V binding (FIG. 6(B)) in primary striatal neurons co-cultured with astrocytes activated by exposure to MPTP and TNF-α/IFN-γ. Co-treatment of astrocytes with DIM-C-pPhtBu prior to incubation with neurons suppressed neuronal apoptosis. Quantitation of fluorescence intensity demonstrates elevated neuronal (FIG. 6(C)) caspase and (FIG. 6(D)) annexin V binding following co-culture with astrocytes challenged with MPTP and TNF-α/IFN-γ, and suppression of this effect by co-treating astrocytes with DIM-C-pPhtBu, rosiglitazone, or the NOS2 inhibitor, AMT. Co-culture experiments were performed three times (n=3), and between 4-6 images captured per replicate for internal repetition.

The efficacy of DIM-C-pPhtBu in preventing astrocyte-dependent neuronal apoptosis was examined in FIG. 6. Astrocytes were grown to confluence in cell culture inserts that are permeable to small molecules but prevent direct cell-cell contact. Following treatment of astrocytes with MPTP and TNF-α/IFN-γ in the presence or absence of DIM-C-pPhtBu (10 µM), rosiglitazone (10 µM), the NOS2 inhibitor AMT (25 nM), or DMSO, astrocytes were washed with PBS and co-incubated directly above primary striatal neurons in neurobasal medium. Indices of neuronal apoptosis were then measured using live-cell fluorescence imaging of caspase activity (FIG. 6A) and Annexin V binding (FIG. 6B). Quantification of caspase activity and Annexin V-binding indicated that astrocytes treated with MPTP and TNF-α/IFN-γ caused apoptosis in co-cultured striatal neurons that was prevented by prior co-treatment of the astrocytes with DIM-C-pPhtBu, rosiglitazone, or AMT (FIG. 6, C-D). The DMSO vehicle control had no suppressive effect.

Example 8

Dose-dependent Expression of NOS2 and Protein Nitration by DIM-C-pPhOCH3 in Primary Cultured Astrocytes.

Figure 7:
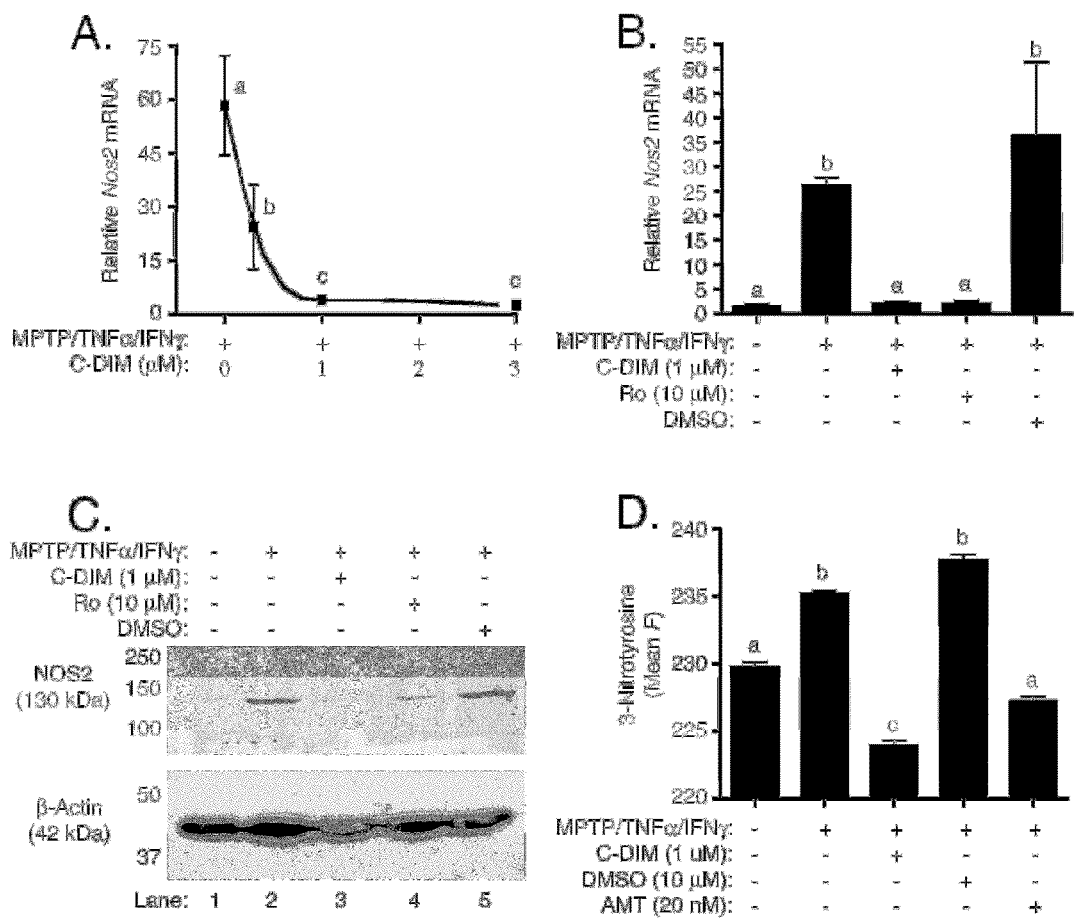
FIG. 7 shows dose-dependent expression of NOS2 and protein nitration by DIM-C-pPhOCH$_3$ in primary cultured astrocytes.

FIG. 7 shows dose-dependent expression of NOS2 and protein nitration by DIM-C-pPhOCH$_3$ in primary cultured astrocytes. FIG. 7(A) shows semi-quantitative real-time RT-PCR demonstrating dose-responsive suppression of Nos2 mRNA by concentrations of DIM-C-pPhOCH$_3$ ranging from 0.1 to 3 µM in astrocytes challenged with MPTP, TNF-α, and IFN-γ. FIG. 7(B) shows semi-quantitative real-time PCR demonstrating equivalent suppression of Nos2 mRNA by either DIM-C-pPhOCH$_3$ or rosiglitazone in astrocytes challenged with MPTP, TNF-α, and IFN-γ. FIG. 7(C) shows that immunoblotting demonstrates suppression of NOS2 protein expression by either DIM-C-pPhOCH$_3$ or rosiglitazone in astrocytes exposed to MPTP and TNF-α/IFN-γ. FIG. 7(D) shows that treatment with DIM-C-pPhOCH$_3$ or the NOS2 inhibitor, AMT, prevents protein nitration in primary astrocytes induced by MPTP and TNF-α/IFN-γ. Differing letters denote statistical significance (p<0.05).

Example 9

Treatment With DIM-C-pPhOCH$_3$ Blocks Activation of NF-kB in Primary Astrocytes.

Figure 8:
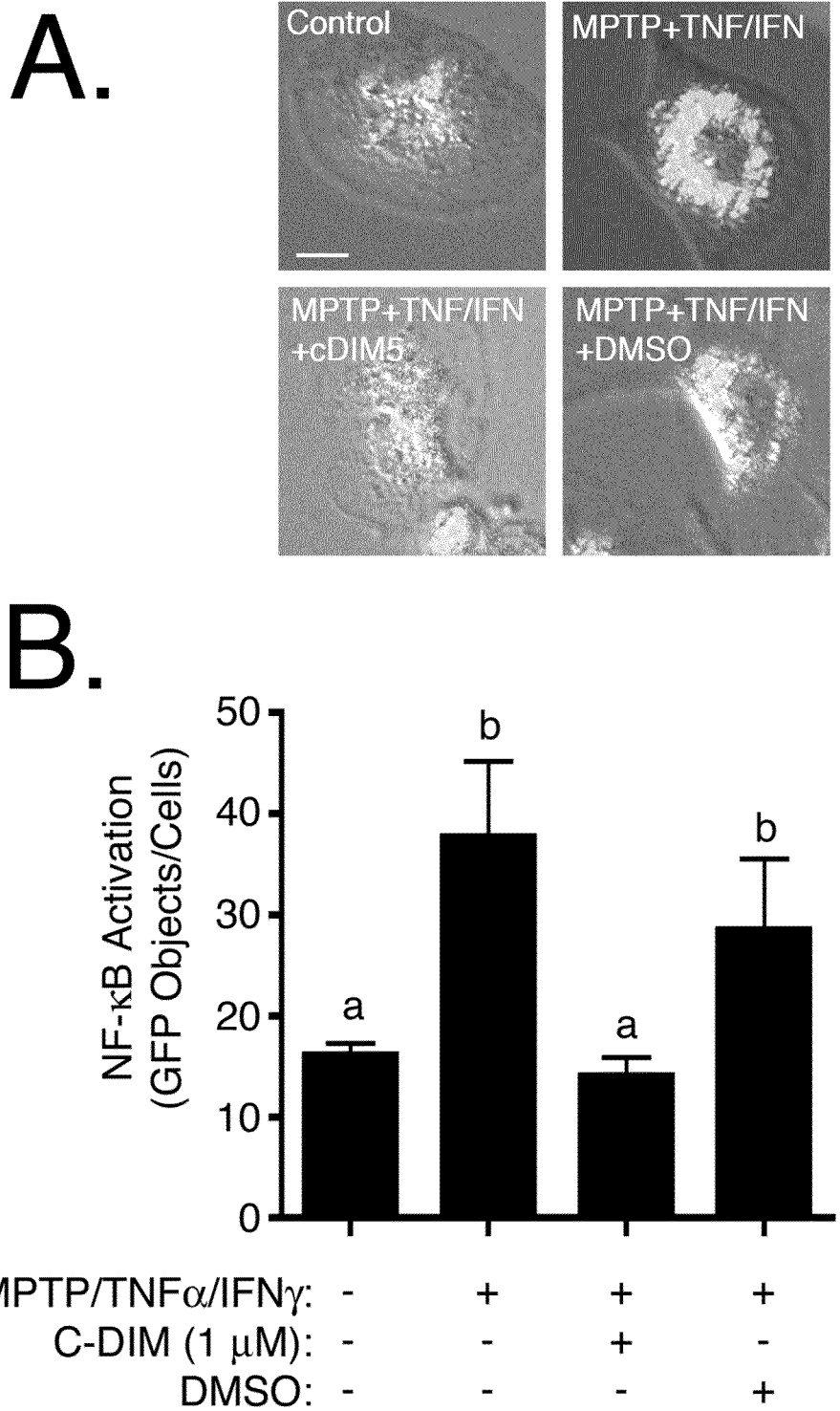
FIG. 8 shows that treatment with DIM-C-pPhOCH$_3$ blocks activation of NF-kB in primary astrocytes.

FIG. 8(A) shows transgenic astrocytes expressing an NF-kB-GFP reporter construct were exposed to MPTP and TNF-α/IFN-γ in the absence or presence of 1 uM DIM-C-pPhOCH$_3$ or vehicle control (DMSO) showing blocked activation. FIG. 8(B) demonstrates that quantitative analysis of GFP fluorescence indicates that DIM-C-pPhOCH$_3$ completely abrogated MPTP- and cytokine-induced activation of NF-kB. Differing letters denote statistical significance (p<0.05).

Example 10

DIM-C-pPhOCH$_3$ Treatment Modulates Nuclear Co-Repressor Interactions With NF-kB Binding Sites in the Nos2 Promoter.

Figure 9:
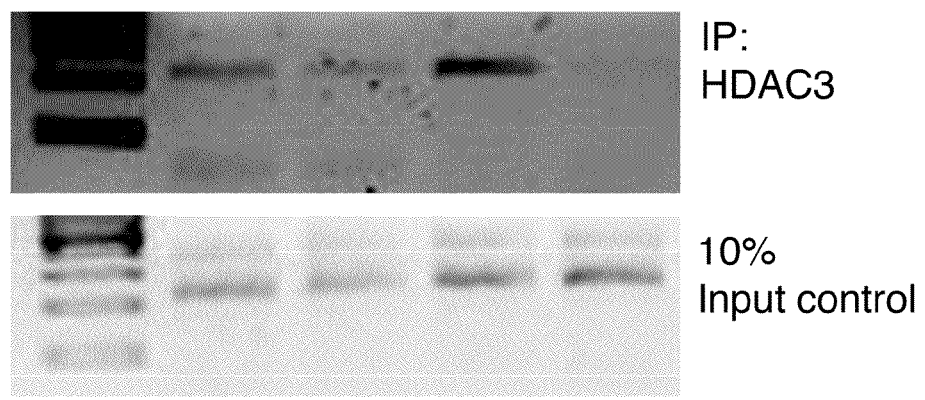
FIG. 9 shows that DIM-C-pPhOCH$_3$ treatment modulates nuclear co-repressor interactions with NF-kB binding sites in the Nos2 promoter. Primary cultured astrocytes were treated with MPTP and TNF/IFN in the presence or absence of DIM-C-pPhOCH$_3$ (DIM5, 1 uM) or rosiglitazone (Ro, 10 uM) and cellular lysates subjected to chromatin immunoprecipitation (ChIP) assay for HDAC3 association with the proximal NF-kB binding site in the Nos2 promoter. HDAC3 is a transcriptional co-repressor of Nos2 gene expression. DIM-C-pPhOCH3, but not Ro, increased association of HDAC3 with the NF-kB binding site, indicating recruitment of co-repressor proteins as a likely distinct mechanistic target of DIM-C-pPhOCH3.

Primary cultured astrocytes were treated with MPTP and TNF/IFN in the presence or absence of DIM-C-pPhOCH$_3$ (DIMS, 1 uM) or rosiglitazone (Ro, 10 uM) and cellular lysates subjected to chromatin immunoprecipitation (ChIP) assay for HDAC3 association with the proximal NF-kB binding site in the Nos2 promoter. HDAC3 is a transcriptional co-repressor of Nos2 gene expression. DIM-C-pPhOCH3, but not Ro, increased association of HDAC3 with the NF-kB binding site, indicating recruitment of co-repressor proteins as a likely distinct mechanistic target of DIM-C-pPhOCH3. See FIG. 9.

Example 11

In vitro Neuroprotective Efficacy of DIM-C-pPhOCH$_3$.

Figure 10:
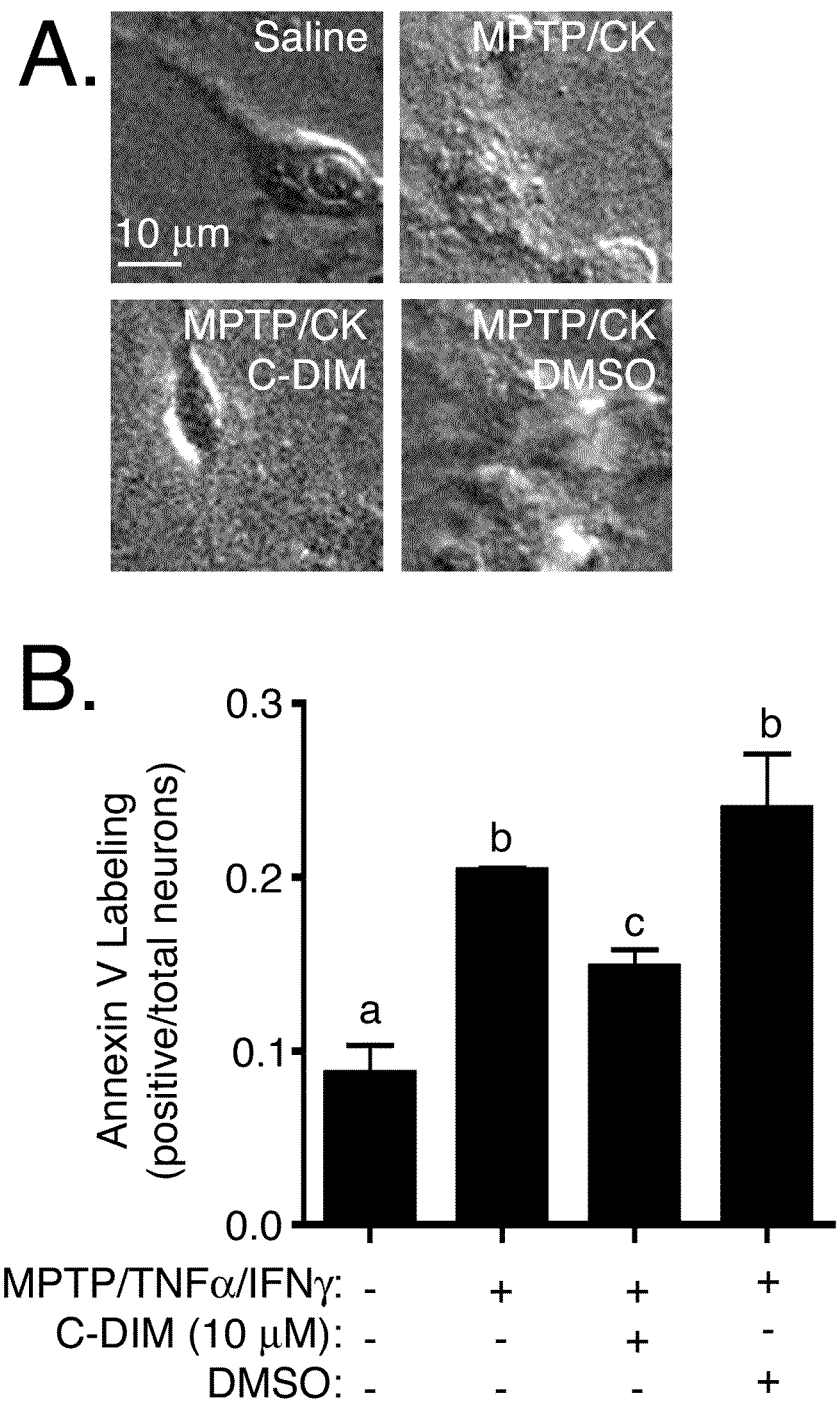
FIG. 10 shows in vitro neuroprotective efficacy of DIM-C-pPhOCH$_3$.

FIG. 10(A) shows primary cultured astrocytes plated on permeable transwell inserts were treated with MPTP and TNF/IFN in the presence or absence of DIM-C-pPhOCH$_3$ (DIMS, 1 uM) or vehicle (DMSO) for 24 hrs, washed, and then incubated with primary striatal neurons cultured on glass cover slips for 6 hrs Annexin IV binding was assessed in neurons by live-cell fluorescence imaging as a measure of apoptotic cell death (red fluorescence). MPTP and cytokine (CK) treatment increased Annexin IV binding that was inhibited by DIM-C-pPhOCH₃. FIG. 10(B) shows that quantitative determination of Annexin IV fluorescence indicates that DIM-C-pPhOCH₃ significantly reduced activation of astrocytes and subsequent neuronal apoptosis. Differing letters denote statistical significance ($p<0.05$).

Example 12

DIM-C-pPhOCH₃ Suppresses Activation of a Broad Array of NF-kB-regulated Genes in Primary Astrocytes.

Figure 11B:
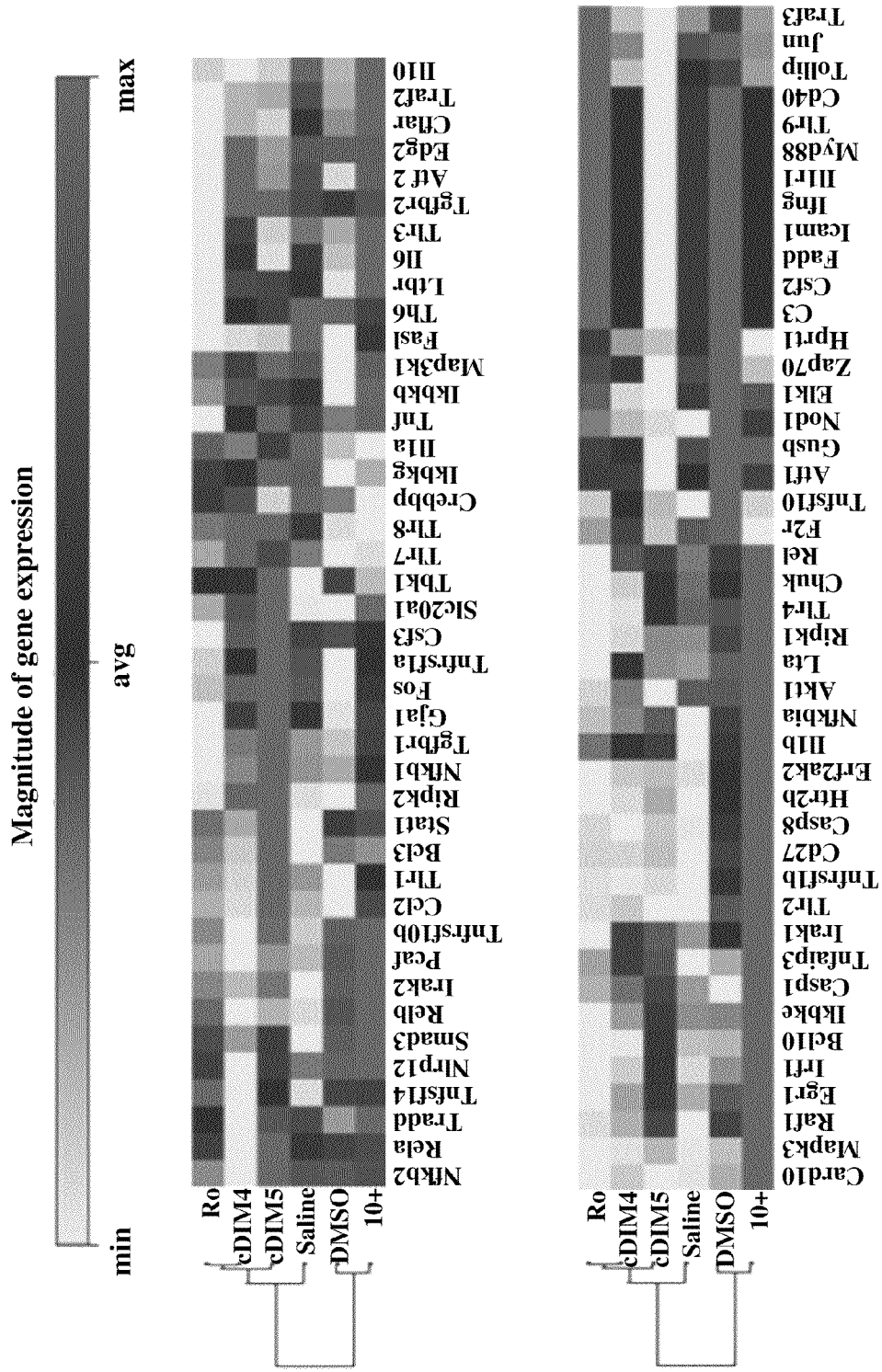
FIG. 11(B) shows a heat map and cluster analysis (ontology tree, top) indicating that both DIM-C-pPhtBu and DIM-C-pPhOCH$_3$ segregated with the saline-treated control, demonstrating suppression of inflammatory genes through the NF-kB pathway. (n=4 biological replicates)

Expression of inflammatory genes in astrocytes is largely regulated through the NF-kB signaling pathway. Primary cultured astrocytes were treated with MPTP and TNF/IFN in the presence or absence DIM-C-pPhOCH₃ (DIMS, 1 uM), DIM-C-pPhtBu (DIM4), rosiglitazone (Ro, 10 uM), or vehicle (DMSO) and subjected to qPCR array analysis of NF-kB-regulated transcripts (Superarray Biosciences). FIG. 11(A) shows representative NF-kB-regulated genes depicted in tabular format, indicating that both DIM-C-pPhtBu and DIM-C-pPhOCH₃ suppressed neuroinflammatory gene expression of such transcripts as TNF Receptor, Toll Receptor, and Interleukin 1beta. FIG. 11(B) shows a heat map and cluster analysis (ontology tree, top) indicating that both DIM-C-pPhtBu and DIM-C-pPhOCH₃ segregated with the saline-treated control, demonstrating suppression of inflammatory genes through the NF-kB pathway. (n=4 biological replicates)

Example 13

Anti-inflammatory Efficacy of DIM-C-pPhtBu (DIM4) in Mice Treated with MPTP.

Figure 12:
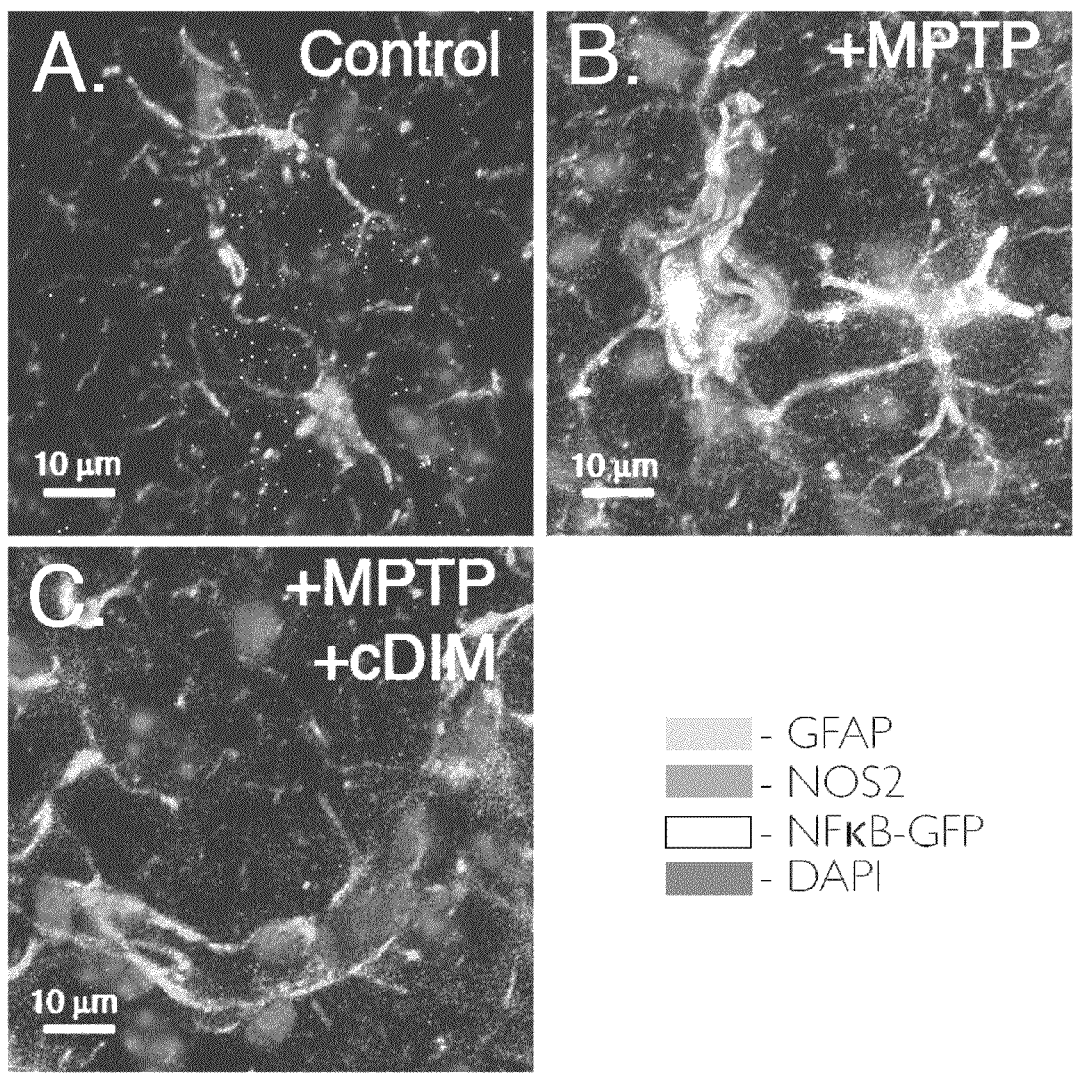
FIG. 12 shows anti-inflammatory efficacy of DIM-C-pPhtBu (DIM4) in mice treated with MPTP. Transgenic NF-kB-GFP reporter mice (C57B1/6 background) were exposed to MPTP (2 injections of 15 mg/Kg, 12 hours apart) in the presence and absence of DIM-C-pPhtBu and assessed for activation of astrocytes, expression of NOS2, and expression of GFP (representing NF-kB activity). DIM-C-pPhtBu was administered once per day for four days following MPTP treatment by oral gavage in corn oil at 50 mg/kg and frozen sections through the striatum were prepared 7 days following MPTP. Immunofluorescence images were collected using a 40× Zeiss PlanApochromat objective for GFAP as a marker for astrocytes (purple), NOS2 (red), green fluorescent protein (GFP; green), and DAPI (blue; DNA stain). Co-location of red and green channels is depicted in the image as yellow.

Transgenic NF-κB-GFP reporter mice (C57B1/6 background) were exposed to MPTP (2 injections of 15 mg/kg, 12 hours apart) in the presence and absence of DIM-C-pPhtBu and assessed for activation of astrocytes, expression of NOS2, and expression of GFP (representing NF-kB activity). DIM-C-pPhtBu was administered once per day for four days following MPTP treatment by oral gavage in corn oil at 50 mg/Kg and frozen sections through the striatum were prepared 7 days following MPTP. Immunofluorescent images were collected using a 40× Zeiss PlanApochromat objective for GFAP as marker for astrocytes (purple), NOS2 (red), green fluorescent protein (GFP; green), and DAPI (blue; DNA stain). Co-location of red and green channels is depicted in the image as yellow. FIG. 12(A) shows that control animals did not display activation of astrocytes or expression of either NOS2 or NF-kB at significant levels. FIG. 12(B) shows that MPTP treatment induced marker hypertrophic activation of astrocytes that expressed both NOS2 and NF-κB/GFP. This activated glial phenotype was inhibited by treatment with DIM-C-pPhtBu.

Example 14

DIM-C-pPhOCH₃ Prevented Protein Nitration in Dopaminergic Neurons in Mice Treated with MPTP.

Figure 13:
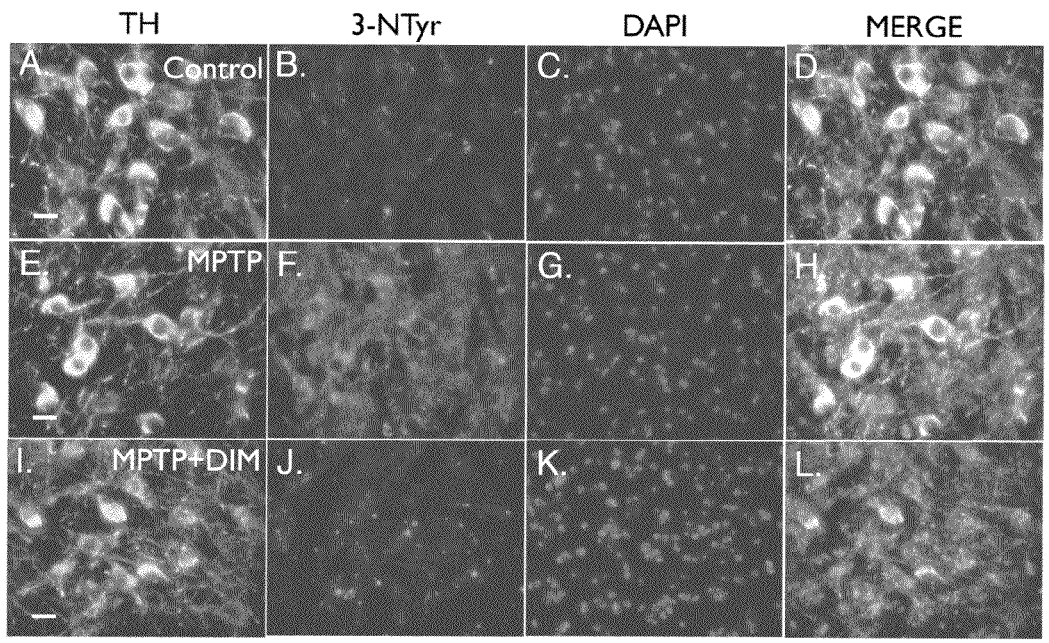
FIG. 13 shows that DIM-C-pPhOCH$_3$ prevented protein nitration in dopaminergic neurons in mice treated with MPTP. C57Bl/6 mice were treated with MPTP (2 injections of 15 mg/kg, 12 hours apart) in the presence and absence of DIM-C-pPhOCH$_3$ (DIM5) and assessed for 3-nitrotyrosine protein adducts (a maker of nitrosative stress and excessive NO/peroxynitrite formation). DIM-C-pPhOCH$_3$ was administered once per day for four days following MPTP treatment by oral gavage in corn oil at 50 mg/Kg and frozen sections through the substantia nigra were prepared 7 days following MPTP. Immunofluorescence images were collected using a 40× Zeiss PlanApochromat objective for tyrosine hydroxylase (green), 3-nitrotyrosine (red), and DAPI (blue; DNA/nuclear stain). Protein nitration in dopaminergic neurons was barely detectable in control animals (FIG. 13(A-D)) but was dramatically increased in MPTP mice (FIG. 13(E-F)). DIM-C-pPhOCH$_3$ completely suppressed protein nitration (I-L and M; quantitative), indicating blockade of neuroinflammation.
Figure 13:
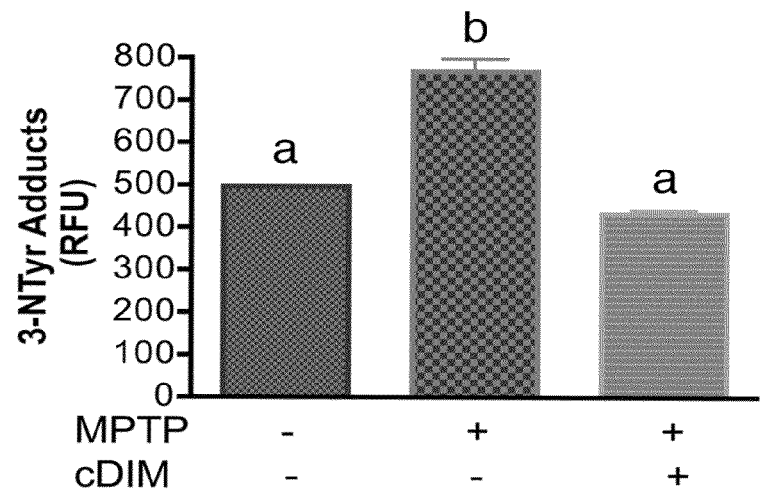

C57B1/6 mice were treated with MPTP (2 injections of 15 mg/kg, 12 hours apart) in the presence and absence of DIM-C-pPhOCH₃ (DIM5) and assessed for 3-nitrotyrosine protein adducts (a marker of nitrosative stress and excessive NO/peroxynitrite formation). DIM-C-pPhOCH₃ was administered once per day for four days following MPTP treatment by oral gavage in corn oil at 50 mg/Kg and frozen sections through the substantia nigra were prepared 7 days following MPTP. Immunofluorescence images were collected using a 40× Zeiss PlanApochromat objective for tyrosine hydroxylase (green), 3-nitrotyrosine (red), and DAPI (blue; DNA/nuclear stain). Protein nitration in dopaminergic neurons was barely detectable in control animals (FIG. 13(A-D)) but was dramatically increased in MPTP mice (FIG. 13(E-F)). DIM-C-pPhOCH₃ completely suppressed protein nitration (I-L and M; quantitative), indicating blockade of neuroinflammation. DIM-C-pPhOCH₃ prevented protein nitration in dopaminergic neurons in mice treated with MPTP.

It will be apparent to those skilled in the art that various modifications and variations can be made in the methods and compositions of the present invention without departing from the spirit or scope of the invention.

The invention claimed is:

1. A method for treating Parkinson's disease in a subject, comprising administering to the subject a therapeutically effective amount of a composition comprising a compound selected from the group consisting of: 1,1-bis(3'-indolyl)-1-(p-chlorophenyl)methane, 1,1-bis(3'-indolyl)-1-(p-methoxyphenyl)methane, 1,1-bis(3'-indolyl)-1-(p-bromophenyl)methane, and 1,1-bis(3'-indolyl)-1-(p-fluorophenyl)methane,
   or a pharmaceutically acceptable salt or stereoisomer thereof.

2. The method of claim 1, wherein the compound comprises 1,1-bis(3'-indolyl)-1-(p-chlorophenyl)methane, or a pharmaceutically acceptable salt or stereoisomer thereof.

3. The method of claim 1, wherein the compound comprises 1,1-bis(3'-indolyl)-1-(p-methoxyphenyl)methane, or a pharmaceutically acceptable salt or stereoisomer thereof.

4. The method of claim 1, wherein the compound comprises 1,1-bis(3'-indolyl)-1-(p-bromophenyl)methane, or a pharmaceutically acceptable salt or stereoisomer thereof.

5. The method of claim 1, wherein the compound comprises 1,1-bis(3'-indolyl)-1-(p-fluorophenyl)methane, or a pharmaceutically acceptable salt or stereoisomer thereof.

\* \* \* \* \*

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
tcacgcttgg gtcttgtt                                                 18

<210> SEQ ID NO 2
<211> LENGTH: 21
<212> TYPE: DNA
<213> ORGANISM: Artificial Sequence
<220> FEATURE:
<223> OTHER INFORMATION: Synthetic Construct

<400> SEQUENCE: 2
caggtcactt tggtaggatt t                                             21

```
-continued

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
gctgtgctat gttgctctag                                                   20

<210> SEQ ID NO 4
<211> LENGTH: 18
<212> TYPE: DNA
<213> ORGANISM: Artificial Sequence
<220> FEATURE:
<223> OTHER INFORMATION: Synthetic Construct

<400> SEQUENCE: 4
cgctcgttgc caatactg                                                     18

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
atggccttgc atgaggatac acca                                              24

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct

<400> SEQUENCE: 6
gagtctcagt cttcaactcc ctgt                                              24
```